United States Patent
Kondoh

(10) Patent No.: US 9,693,755 B2
(45) Date of Patent: Jul. 4, 2017

(54) ULTRASOUND DIAGNOSTIC DEVICE AND METHOD FOR CONTROLLING ULTRASOUND DIAGNOSTIC DEVICE

(71) Applicant: KONICA MINOLTA, INC., Chiyoda-ku, Tokyo (JP)

(72) Inventor: Youichi Kondoh, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 319 days.

(21) Appl. No.: 14/373,297

(22) PCT Filed: Jan. 10, 2013

(86) PCT No.: PCT/JP2013/000047
§ 371 (c)(1),
(2) Date: Jul. 18, 2014

(87) PCT Pub. No.: WO2013/108592
PCT Pub. Date: Jul. 25, 2013

(65) Prior Publication Data
US 2014/0371593 A1    Dec. 18, 2014

(30) Foreign Application Priority Data
Jan. 19, 2012 (JP) ................ 2012-008858

(51) Int. Cl.
*A61B 8/08* (2006.01)
*A61B 8/14* (2006.01)
*A61B 8/00* (2006.01)

(52) U.S. Cl.
CPC .......... *A61B 8/5223* (2013.01); *A61B 8/0858* (2013.01); *A61B 8/0891* (2013.01);
(Continued)

(58) Field of Classification Search
None
See application file for complete search history.

(56) References Cited

U.S. PATENT DOCUMENTS

2007/0149877 A1   6/2007  Oshiki et al.
2011/0246129 A1   10/2011  Ishikawa et al.
2012/0296214 A1*  11/2012  Urabe .................. A61B 8/0858
                                                   600/444

FOREIGN PATENT DOCUMENTS

JP   2002125971 A   5/2002
JP   2004305377 A   11/2004
(Continued)

OTHER PUBLICATIONS

"maxIMT Measurement: What is the carotid artery bulb region?", Sep. 9, 2010, URL: "www.imt-ca.com/contents/e08.html".
(Continued)

*Primary Examiner* — Katherine Fernandez
(74) *Attorney, Agent, or Firm* — Holtz, Holtz & Volek PC

(57) ABSTRACT

An ultrasound diagnostic device for measuring a carotid artery wall property includes a transmission-reception processor, a transverse cross-sectional image generator, a transverse cross-sectional image selector, and a relative angle calculator. The transmission-reception processor performs transmission and reception processing of ultrasound with respect to the carotid artery. The transverse cross-sectional image generator generates transverse cross-sectional images based on reception signals for carotid artery cross-sections at different positions. Each generated image depicts a carotid artery transverse cross-section perpendicular to a longitudinal direction. The transverse cross-sectional image selector selects a specific image among the generated images that depicts ICA and ECA cross-sections. The relative angle calculator calculates relative angle of the ultrasound probe with respect to the carotid artery in a plane parallel to the carotid artery transverse cross-section, based on coordinates of the ICA and ECA cross-sections in the specific image.

22 Claims, 17 Drawing Sheets

(52) U.S. Cl.
CPC .............. *A61B 8/14* (2013.01); *A61B 8/4461* (2013.01); *A61B 8/463* (2013.01); *A61B 8/469* (2013.01); *A61B 8/483* (2013.01); *A61B 8/485* (2013.01)

(56) References Cited

FOREIGN PATENT DOCUMENTS

| | | |
|---|---|---|
| JP | 2006115937 A | 5/2006 |
| JP | 2011104194 A | 6/2011 |
| WO | 2008023618 A1 | 2/2008 |
| WO | WO 2011/074271  * | 6/2011 |

OTHER PUBLICATIONS

International Search Report dated Feb. 5, 2013 issued in International Application No. PCT/JP2013/000047.
Stein J. H., et al., "Use of Carotid Ultrasound to Identify Subclinical Vascular Disease and Evaluate Cardiovascular Disease Risk: A Consensus Statement from the American Society of Echocardiography Carotid Intima-Media Thickness Task Force Endorsed by the Society for Vascular Medicine", Journal of the American Society of Echocardiography, Feb. 2008, pp. 93-111 (in English).
Chinese Office Action (and English translation thereof) dated Jun. 3, 2015, issued in counterpart Chinese Application No. 201380005927.8.

* cited by examiner

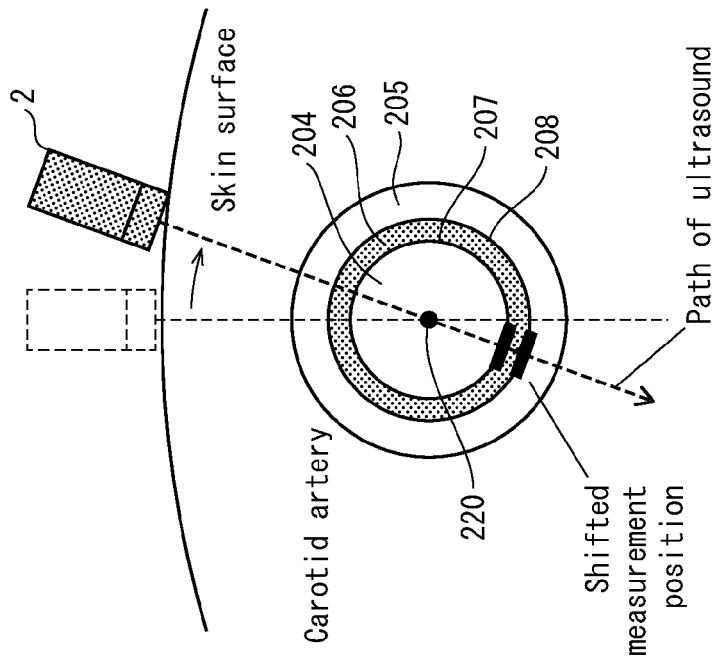
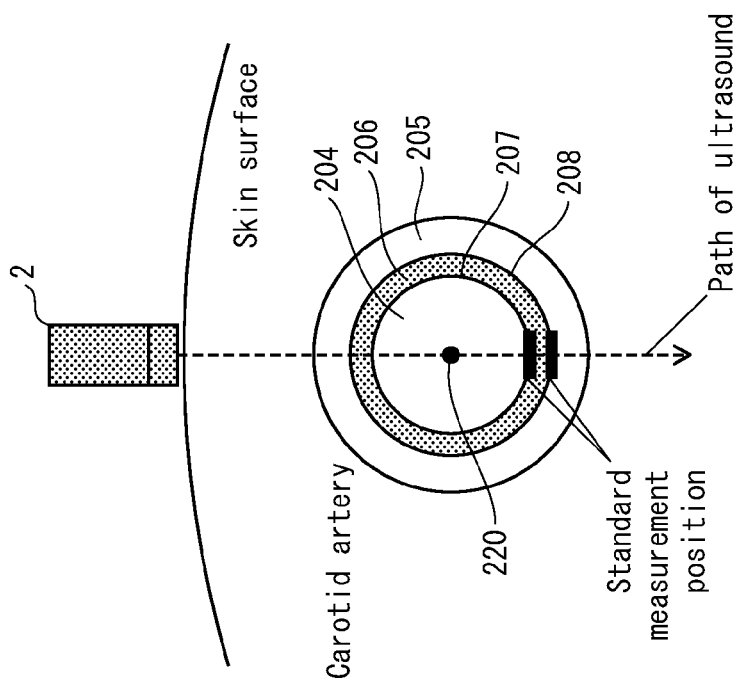

ULTRASOUND DIAGNOSTIC DEVICE AND METHOD FOR CONTROLLING ULTRASOUND DIAGNOSTIC DEVICE

TECHNICAL FIELD

The present invention relates to an ultrasound diagnostic device and a method for controlling an ultrasound diagnostic device, and in particular relates to an art of early-stage diagnosis of arteriosclerosis through carotid artery examination.

BACKGROUND ART

In recent years an increasing number of patients have been suffering from circulatory system related diseases, including ischemic diseases such as myocardial and cerebral infarction. In order to prevent such diseases it is important to detect symptoms of arteriosclerosis and administer treatment at an early stage.

Thickness of an intima-media complex in the carotid artery (herein, referred to as intima-media thickness or abbreviated as IMT) is attracting attention as an indicator which can be used in diagnosis of arteriosclerosis. IMT is an important indicator of early-stage atherosclerosis in the carotid artery.

FIG. 14 is a cross-sectional diagram illustrating a cross-section of the carotid artery in a direction in which the carotid artery extends (herein, referred to as a longitudinal cross-section). The carotid artery is a blood vessel that consists of a vascular wall 201 and a lumen 204. The vascular wall 201 is composed of a tunica intima 202, a tunica media 203, and a tunica adventitia 205 in respective order in a direction outwards from the lumen 204. The term IMT refers to thickness of an intima-media complex 206, which is a complex of the tunica intima 202 and the tunica media 203. An ultrasound diagnostic device can be used in order to visualize the intima-media complex 206 between the lumen 204 and the tunica adventitia 205.

Ultrasound examination can be performed simply and in a non-invasive manner, and therefore is commonly used as a method for measuring IMT. In IMT measurement it is advantageous to use the carotid artery as a measurement target in terms that the carotid artery is particularly susceptible to arteriosclerosis, and also in terms that the carotid artery is located at a relatively shallow depth approximately 2 cm to 3 cm under the skin surface, enabling simple measurement by ultrasound. Measurement of IMT is typically performed based on a two dimensional (2D) image which is an ultrasound diagnostic image orientated along the longitudinal direction of the carotid artery. More specifically, IMT can be measured by detecting an interface between the lumen 204 and the tunica intima 202 illustrated in FIG. 14 (herein, referred to as a lumen-intima interface 207), and an interface between the tunica media 203 and the tunica adventitia 205 illustrated in FIG. 14 (herein, referred to as a media-adventitia interface 208).

FIG. 15 is a perspective diagram illustrating structure of the carotid artery in terms of the longitudinal direction. As illustrated in FIG. 15, the carotid artery is configured by a common carotid artery (herein, abbreviated as "CCA") 213 located at a central end of the carotid artery, and an internal carotid artery (herein, abbreviated as "ICA") 215 and an external carotid artery (herein, abbreviated as "ECA") 216, each located at a peripheral end of the carotid artery. The carotid artery is also configured by a bulb of the common carotid artery (herein, abbreviated as "bulb") 214 which is located between the CCA 213 and each of the ICA 215 and the ECA 216. A bifurcation of the common carotid artery (herein, abbreviated as "bif") 217 is located at a branching point from the bulb 214 to the ICA 215 and the ECA 216.

FIG. 16 is a schematic diagram illustrating a 2D image of the carotid artery orientated along the longitudinal direction. As illustrated in FIG. 16, when an ultrasound diagnostic device is used to measure an IMT measurement range 212, a region of interest (herein, abbreviated as "ROI") 211 is determined which either spans across a vascular wall which is relatively far from the skin surface (herein, referred to as far-side wall 209) or a vascular wall which is relatively close to the skin surface (herein, referred to as near-side wall 210). FIG. 16 illustrates an example in which the ROI 211 is determined such as to span across the far-side wall 209. A section of vascular wall included within the ROI 211 is defined as the IMT measurement range 212, and a value indicating IMT is measured for example as a maximum value of IMT (herein, referred to as max. IMT) or a mean value of IMT (herein, referred to as mean IMT) measured in the IMT measurement range 212. With regards to the IMT measurement range 212, Non-Patent Literature 1 recommends that the IMT measurement range 212 is set as a range which extends for 1 cm towards the CCA 213, starting from a boundary 219 between the CCA 213 and the bulb 214 (herein, referred to as a CCA-bulb boundary 219).

Various methods have been proposed for enabling simple IMT measurement by simplifying a complicated operation of determining the ROI 211, which is used to define the IMT measurement range 212. For example, Non-Patent Literature 2 proposes a method for setting an IMT measurement range in which an inflection point at the CCA-bulb boundary 219 between the CCA 213 and the bulb 214 is detected, and an IMT measurement range is set using the inflection point as a reference.

CITATION LIST

Non-Patent Literature

[Non-Patent Literature 1] Journal of the American Society of Echocardiography; February 2008; pp. 93-111

[Non-Patent Literature 2] Research Group for Early Arteriosclerosis, "maxIMT Measurement", [online], Sep. 9, 2010 (retrieved Sep. 30 2011), URL: "www.imt-ca.com/contents/e08.html"

SUMMARY OF INVENTION

Technical Problem

Due to the nature of arteriosclerosis, it is necessary to perform IMT measurement periodically, and preferably IMT measurement should be performed at the same position during each measurement in order to ensure accurate diagnosis.

FIG. 17 is a schematic diagram illustrating a situation in which an ultrasound probe is applied against the skin of a subject, in proximity to a carotid artery, during measurement of a property of a vascular wall of the carotid artery using an ultrasound diagnostic device. In order to perform accurate diagnosis through measurement at the same measurement position, it is necessary for the ultrasound probe to be applied at a suitable position along the carotid artery of the subject. It is also necessary that the ultrasound probe is applied against the skin such that an angle of the ultrasound probe centered on the carotid artery of the subject is a preset suitable angle. If variation occurs in the angle of the ultrasound probe centered on the carotid artery, it is difficult during each IMT measurement to emit ultrasound towards the same position in a cross-section of the vascular wall of the carotid artery which is perpendicular to the longitudinal direction (herein, referred to as a transverse cross-section).

Herein, the term transverse cross-section refers to a vascular cross-section that exists in a plane extending in a direction in which ultrasound is transmitted from the ultrasound probe (herein, referred to as a depth direction), which is perpendicular to the longitudinal direction of the carotid artery, and also extending in a direction which is perpendicular to both the depth direction and the longitudinal direction of the carotid artery (herein, referred to as a transverse direction).

FIGS. 18A and 18B are cross-sectional schematic diagrams illustrating positional relationship of the ultrasound probe and the carotid artery in terms of the transverse direction. FIG. 18A illustrates a situation in which a central axis of the ultrasound probe matches a vascular center of the carotid artery, and FIG. 18B illustrates a situation in which the central axis of the ultrasound probe is at a shifted angle relative to the vascular center of the carotid artery. In the situation illustrated in FIG. 18A, an ultrasound probe 2 is positioned in a direction directly above a central axis 220 of the carotid artery, and when ultrasound is emitted perpendicularly towards the carotid artery, IMT measurement can be performed on a far-side wall in a longitudinal cross-section perpendicular to the skin surface, which is a standard measurement position for IMT. On the other hand, in the situation illustrated in FIG. 18B, the ultrasound probe 2 is for example at a position shifted to the right relative to the central axis 220 of the carotid artery, and when ultrasound is emitted at an oblique angle towards the carotid artery, IMT is measured in a section of the vascular wall which is shifted to the left relative to the far-side wall in the longitudinal cross-section perpendicular to the skin surface. As described above, when variation occurs in the angle of the ultrasound probe centered on the carotid artery, measurement position becomes shifted such that IMT measurement cannot be performed at the same position in the vascular wall during each measurement.

Non-Patent Literature 2 relates to a method for determining an IMT measurement range at a predetermined position in a vascular wall in a longitudinal cross-section of a carotid artery, and does not relate to a method for determining an IMT measurement range at a suitable position in the vascular wall in a transverse cross-section of the carotid artery. Consequently, the method disclosed in Non-Patent Literature 2 cannot be used in order to set an IMT measurement range at the same position during each measurement of IMT, at least in terms of position in the transverse direction, and therefore the aforementioned method is not sufficient to ensure that an accurate diagnosis is always possible.

Also note that position and shape of a carotid artery may vary between different subjects. Furthermore, even for the same subject, variation in position of a carotid artery may occur depending on condition of a neck of the subject, for example in terms of bending in an upwards, downwards, or sideways direction. There is demand for a method which takes into account the aforementioned variations and sets an IMT measurement range at a predetermined position in a vascular wall in a transverse cross-section of the carotid artery.

The present invention solves the conventional problem described above, and an objective thereof is to provide an ultrasound diagnostic device, and a method for controlling an ultrasound diagnostic device, which sets an IMT measurement range at a predetermined position in a vascular wall in a carotid artery transverse cross-section.

Solution to Problem

In order to achieve the objective described above, one aspect of the present invention relates to an ultrasound diagnostic device which is for measuring a property of a vascular wall of a carotid artery and to which an ultrasound probe is connectable, the ultrasound diagnostic device comprising: a transmission-reception processor that performs transmission processing to supply a transmission signal to the ultrasound probe in order to drive the ultrasound probe to transmit ultrasound along a carotid artery cross-section at each of a plurality of positions along a direction perpendicular to the carotid artery cross-section, and that performs reception processing to generate a reception signal for the carotid artery cross-section at each of the positions, based on ultrasound reflected from the carotid artery and received by the ultrasound probe; a transverse cross-sectional image generator that generates a plurality of transverse cross-sectional images based on reception signals respectively generated at the positions, each of the transverse cross-sectional images depicting a carotid artery transverse cross-section that is perpendicular to a longitudinal direction of the carotid artery; a transverse cross-sectional image selector that selects, as a specific image from among the transverse cross-sectional images which are generated, a transverse cross-sectional image that depicts an internal carotid artery cross-section and an external carotid artery cross-section; and a relative angle calculator that calculates a relative angle of the ultrasound probe with respect to the carotid artery in a plane parallel to the carotid artery transverse cross-section, based on coordinates at which the internal carotid artery cross-section and the external carotid artery cross-section are depicted in the specific image.

Furthermore, another aspect of the present invention relates to a method for controlling an ultrasound diagnostic device which is for measuring a property of a vascular wall of a carotid artery and to which an ultrasound probe is connectable, the method comprising: performing transmission processing to supply a transmission signal to the ultrasound probe in order to drive the ultrasound probe to transmit ultrasound along a carotid artery cross-section at each of a plurality of positions along a direction perpendicular to the carotid artery cross-section, and performing reception processing to generate a reception signal for the carotid artery cross-section at each of the positions, based on ultrasound reflected from the carotid artery and received by the ultrasound probe; generating a plurality of transverse cross-sectional images based on reception signals respectively generated at the positions, each of the transverse cross-sectional images depicting a carotid artery transverse cross-section that is perpendicular to a longitudinal direction of the carotid artery; selecting, as a specific image from among the transverse cross-sectional images which are generated, a transverse cross-sectional image that depicts an internal carotid artery cross-section and an external carotid artery cross-section; and calculating a relative angle of the ultrasound probe with respect to the carotid artery in a plane parallel to the carotid artery transverse cross-section, based on coordinates at which the internal carotid artery cross-section and the external carotid artery cross-section are depicted in the specific image.

Advantageous Effects of Invention

Through the configuration described above, the present invention enables appropriate measurement and management of the relative angle of the ultrasound probe in the plane parallel to the carotid artery transverse cross-section while the ultrasound is applied against skin surface at the nape of the neck. Consequently, a measurement range can be set at the same position in the transverse cross-section during each measurement. Therefore, accurate measurement of a property of the vascular wall such as IMT can be performed during each measurement, enabling accurate diagnosis.

BRIEF DESCRIPTION OF DRAWINGS

FIG. 18A is a cross-sectional schematic diagram illustrating positional relationship of an ultrasound probe and a carotid artery in terms of a transverse direction in a situation in which a central axis of the ultrasound probe matches a vascular center of the carotid artery, and FIG. 18B is a cross-sectional schematic diagram illustrating the aforementioned positional relationship in a situation in which the central axis of the ultrasound probe is positioned at an angle which is shifted relative to the vascular center of the carotid artery.

DESCRIPTION OF EMBODIMENTS

Figure 1:
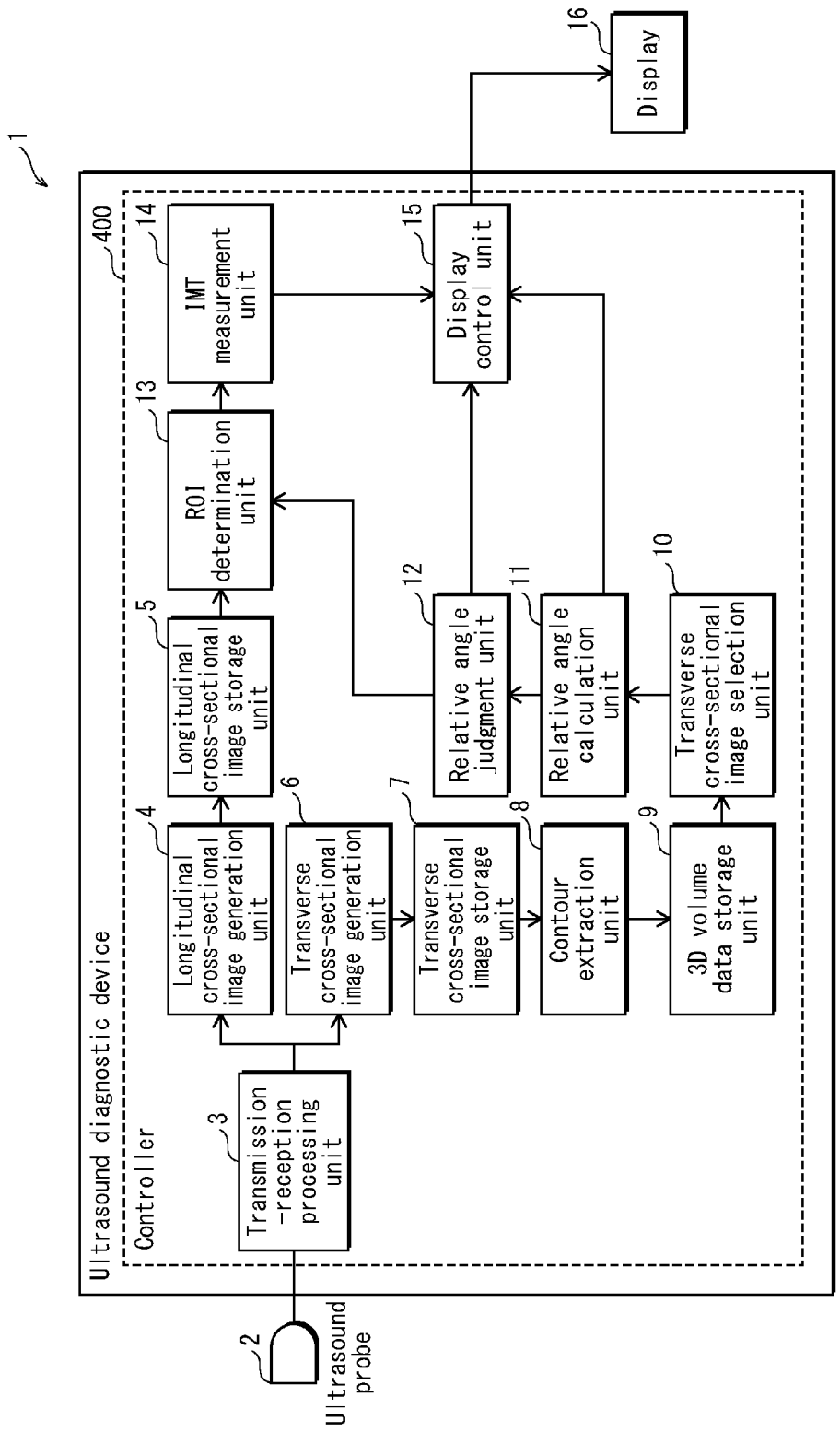
FIG. 1 is a block diagram illustrating functional configuration of an ultrasound diagnostic device 1 relating to a first embodiment.

The following explains, with reference to the drawings, ultrasound diagnostic devices, and methods for controlling an ultrasound diagnostic device, relating to embodiments of the present invention.

<<Summary Of Embodiments>>

One aspect of the present invention is an ultrasound diagnostic device which is for measuring a property of a vascular wall of a carotid artery and to which an ultrasound probe is connectable, the ultrasound diagnostic device comprising: a transmission-reception processor that performs transmission processing to supply a transmission signal to the ultrasound probe in order to drive the ultrasound probe to transmit ultrasound along a carotid artery cross-section at each of a plurality of positions along a direction perpendicular to the carotid artery cross-section, and that performs reception processing to generate a reception signal for the carotid artery cross-section at each of the positions, based on ultrasound reflected from the carotid artery and received by the ultrasound probe; a transverse cross-sectional image generator that generates a plurality of transverse cross-sectional images based on reception signals respectively generated at the positions, each of the transverse cross-sectional images depicting a carotid artery transverse cross-section that is perpendicular to a longitudinal direction of the carotid artery; a transverse cross-sectional image selector that selects, as a specific image from among the transverse cross-sectional images which are generated, a transverse cross-sectional image that depicts an internal carotid artery cross-section and an external carotid artery cross-section; and a relative angle calculator that calculates a relative angle of the ultrasound probe with respect to the carotid artery in a plane parallel to the carotid artery transverse cross-section, based on coordinates at which the internal carotid artery cross-section and the external carotid artery cross-section are depicted in the specific image.

Alternatively, the transverse cross-sectional image selector may further select, as an additional specific image from among the transverse cross-sectional images which are generated, a transverse cross-sectional image that depicts either one of a common carotid artery cross-section and a common carotid artery bulb cross-section, and the relative angle calculator may calculate the relative angle of the ultrasound probe further based on coordinates at which the one of the common carotid artery cross-section and the common carotid artery bulb cross-section is depicted in the additional specific image.

Alternatively, the ultrasound diagnostic device may further comprise a notifier that notifies the relative angle calculated by the relative angle calculator to an operator.

Alternatively, the relative angle calculator may calculate the relative angle of the ultrasound probe based on central coordinates of the internal carotid artery cross-section and central coordinates of the external carotid artery cross-section, or based on the central coordinates of the internal carotid artery cross-section, the central coordinates of the external carotid artery cross-section, and central coordinates of the one of the common carotid artery cross-section and the common carotid artery bulb cross-section.

Alternatively, the transverse cross-sectional image selector may select at least one out of the specific image and the additional specific image using, as a reference, a transverse cross-sectional image that depicts a bifurcation of a common carotid artery.

Alternatively, the transverse cross-sectional image selector may determine the transverse cross-sectional image that depicts the bifurcation of the common carotid artery based on a number of carotid artery transverse cross-sections depicted in each of the plurality of transverse cross-sectional images which are generated.

Alternatively, the ultrasound diagnostic device may further comprise a relative angle judger that performs a judgment of whether the relative angle is a suitable angle.

Alternatively, the relative angle judger may store therein a preset reference angle and may judge that the relative angle is the suitable angle when the relative angle is within a predetermined range of the reference angle.

Alternatively, the ultrasound diagnostic device may further comprise a notifier that notifies results of the judgment performed by the relative angle judger to an operator.

Alternatively, the ultrasound diagnostic device may further comprise: an ROI determiner that, upon the relative angle judger judging that the relative angle is the suitable angle, determines an ROI that defines a measurement range for IMT measurement, using, as a reference, the transverse cross-sectional image that depicts the bifurcation of the common carotid artery; and an IMT measurer that measures IMT as the property of the vascular wall of the carotid artery using a reception signal for a carotid artery cross-section included in the ROI.

Another aspect of the present invention is an ultrasound diagnostic device which is for measuring a property of a vascular wall of a carotid artery and to which an ultrasound probe is connectable, the ultrasound diagnostic device comprising: a transmission-reception processor that performs transmission processing to supply a transmission signal to the ultrasound probe in order to drive the ultrasound probe to transmit ultrasound along a carotid artery cross-section at each of a plurality of positions along a direction perpendicular to the carotid artery cross-section, and that performs reception processing to generate a reception signal for the carotid artery cross-section at each of the positions, based on ultrasound reflected from the carotid artery and received by the ultrasound probe; a transverse cross-sectional image generator that generates a plurality of transverse cross-sectional images based on reception signals respectively generated at the positions, each of the transverse cross-sectional images depicting a carotid artery transverse cross-section that is perpendicular to a longitudinal direction of the carotid artery; a transverse cross-sectional image selector that selects, as a specific image from among the transverse cross-sectional images which are generated, a transverse cross-sectional image that depicts an internal carotid artery cross-section and an external carotid artery cross-section, and that selects, as an additional specific image from among the transverse cross-sectional images which are generated, a transverse cross-sectional image that depicts either one of a common carotid artery cross-section and a common carotid artery bulb cross-section; and a relative angle calculator that calculates a relative angle of the ultrasound probe with respect to the carotid artery in a plane parallel to the carotid artery transverse cross-section, based on coordinates at which either one of the internal carotid artery cross-section and the external carotid artery cross-section is depicted in the specific image, and coordinates at which the one of the common carotid artery cross-section and the common carotid artery bulb cross-section is depicted in the additional specific image.

Another aspect of the present invention is a method for controlling an ultrasound diagnostic device which is for measuring a property of a vascular wall of a carotid artery and to which an ultrasound probe is connectable, the method comprising: performing transmission processing to supply a transmission signal to the ultrasound probe in order to drive the ultrasound probe to transmit ultrasound along a carotid artery cross-section at each of a plurality of positions along a direction perpendicular to the carotid artery cross-section, and performing reception processing to generate a reception signal for the carotid artery cross-section at each of the positions, based on ultrasound reflected from the carotid artery and received by the ultrasound probe; generating a plurality of transverse cross-sectional images based on reception signals respectively generated at the positions, each of the transverse cross-sectional images depicting a carotid artery transverse cross-section that is perpendicular to a longitudinal direction of the carotid artery; selecting, as a specific image from among the transverse cross-sectional images which are generated, a transverse cross-sectional image that depicts an internal carotid artery cross-section and an external carotid artery cross-section; and calculating a relative angle of the ultrasound probe with respect to the carotid artery in a plane parallel to the carotid artery transverse cross-section, based on coordinates at which the internal carotid artery cross-section and the external carotid artery cross-section are depicted in the specific image.

Alternatively, the method may further comprise selecting, as an additional specific image from among the transverse cross-sectional images which are generated, a transverse cross-sectional image that depicts either one of a common carotid artery cross-section and a common carotid artery bulb cross-section, wherein the relative angle of the ultrasound probe may be calculated further based on coordinates at which the one of the common carotid artery cross-section and the common carotid artery bulb cross-section is depicted in the additional specific image.

Alternatively, the method may further comprise notifying the relative angle which is calculated to an operator.

Alternatively, at least one out of the specific image and the additional specific image may be selected using, as a reference, a transverse cross-sectional image that depicts a bifurcation of a common carotid artery, and the method may further comprise: determining, when the relative angle is judged to be a suitable angle, an ROI that defines a measurement range for IMT measurement, using, as a reference, the transverse cross-sectional image that depicts the bifurcation of the common carotid artery; and measuring IMT as the property of the vascular wall of the carotid artery using a reception signal for a carotid artery cross-section included in the ROI.

Another aspect of the present invention is a method for controlling an ultrasound diagnostic device which is for measuring a property of a vascular wall of a carotid artery and to which an ultrasound probe is connectable, the method comprising: performing transmission processing to supply a transmission signal to the ultrasound probe in order to drive the ultrasound probe to transmit ultrasound along a carotid artery cross-section at each of a plurality of positions along a direction perpendicular to the carotid artery cross-section, and performing reception processing to generate a reception signal for the carotid artery cross-section at each of the positions, based on ultrasound reflected from the carotid artery and received by the ultrasound probe; generating a plurality of transverse cross-sectional images based on reception signals respectively generated at the positions, each of the transverse cross-sectional images depicting a carotid artery transverse cross-section that is perpendicular to a longitudinal direction of the carotid artery; selecting, as a specific image from among the transverse cross-sectional images which are generated, a transverse cross-sectional image that depicts an internal carotid artery cross-section and an external carotid artery cross-section, and selecting, as an additional specific image from among the transverse cross-sectional images which are generated, a transverse cross-sectional image that depicts either one of a common carotid artery cross-section and a common carotid artery bulb cross-section; and calculating a relative angle of the ultrasound probe with respect to the carotid artery in a plane parallel to the carotid artery transverse cross-section, based on coordinates at which either one of the internal carotid artery cross-section and the external carotid artery cross-section is depicted in the specific image, and coordinates at which the one of the common carotid artery cross-section and the common carotid artery bulb cross-section is depicted in the additional specific image.

The following provides detailed explanation, with reference to the drawings, of embodiments of an ultrasound diagnostic device and a method for controlling an ultrasound diagnostic device relating to the present invention.

<<First Embodiment>>

The following explains an ultrasound diagnostic device relating to a first embodiment with reference to the drawings.

<Configuration>

(General Configuration)

FIG. 1 is a block diagram illustrating functional configuration of an ultrasound diagnostic device 1 relating to the first embodiment.

The ultrasound diagnostic device 1 is electrically connectable to an ultrasound probe 2 that transmits ultrasound towards a target and receives ultrasound from the target. FIG. 1 illustrates the ultrasound diagnostic device 1 in a connected state with the ultrasound probe 2. The ultrasound diagnostic device 1 includes a controller 400. The controller 400 includes a transmission-reception processing unit 3, a longitudinal cross-sectional image generation unit 4, a longitudinal cross-sectional image storage unit 5, a transverse cross-sectional image generation unit 6, a transverse cross-sectional image storage unit 7, a contour extraction unit 8, a three dimensional (3D) volume data storage unit 9, a transverse cross-sectional image selection unit 10, a relative angle calculation unit 11, a relative angle judgment unit 12, an ROI determination unit 13, an IMT measurement unit 14, and a display control unit 15. Each of the above elements is controlled by a control unit (not illustrated). The display control unit 15 is connected to a display 16.

(Ultrasound Probe 2)

Figure 2:
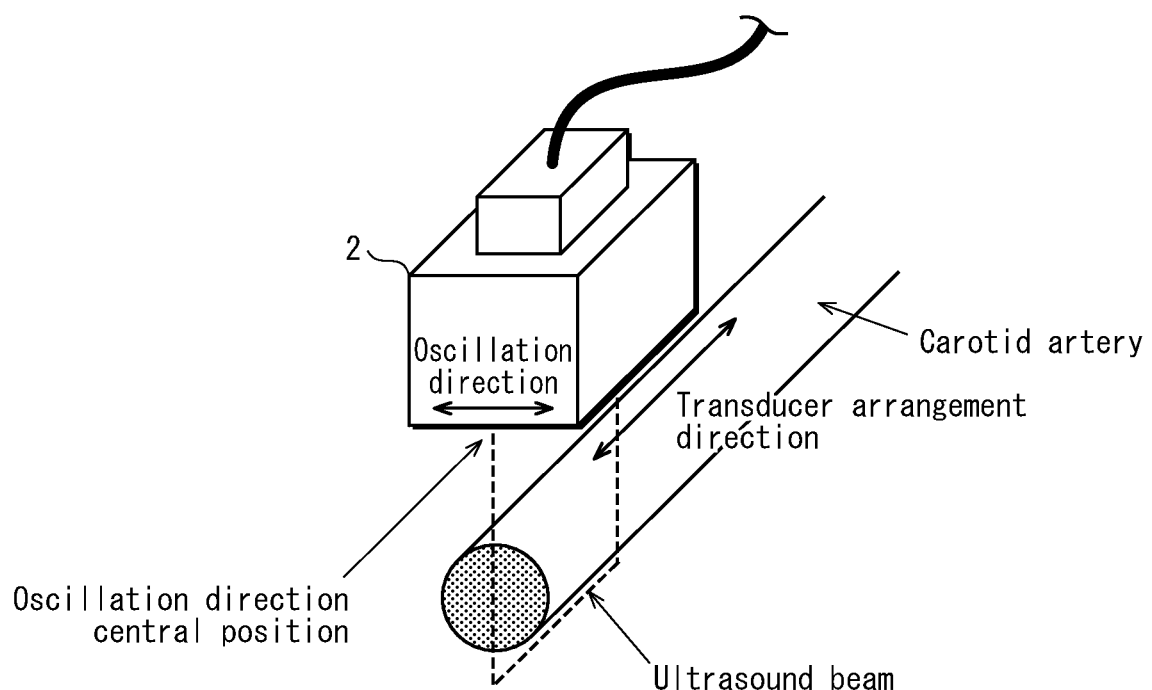
FIG. 2 is a schematic diagram illustrating, for the ultrasound diagnostic device 1 relating to the first embodiment, a situation in which an ultrasound probe 2 is scanned perpendicularly to a longitudinal direction of a carotid artery.

As illustrated in FIG. 2, the ultrasound probe 2 includes a transducer column configured by a plurality of piezoelectric elements arranged in a column along an arrangement direction. The ultrasound probe 2 is a so called oscillating ultrasound probe in which the transducer column is able to mechanically oscillate in a direction perpendicular to the arrangement direction (herein, the aforementioned perpendicular direction is referred to as an oscillation direction).

The ultrasound probe 2 converts a transmission signal supplied from the transmission-reception processing unit 3, which is either a pulse or continuous electrical signal, into pulse or continuous ultrasound. Note that the transmission-reception processing unit 3 is explained further below. With the transducer column applied against skin surface of a subject, the ultrasound probe 2 emits an ultrasound beam from the skin surface towards a carotid artery of the subject. In order to acquire a 2D image depicting a longitudinal cross-section of the carotid artery, an ultrasound beam is emitted while the ultrasound probe 2 is positioned with the transducer column orientated along the carotid artery in a longitudinal direction of the carotid artery. The ultrasound probe 2 subsequently receives an ultrasound echo signal which is ultrasound reflected from the subject, and converts the ultrasound echo signal into an electrical signal through the transducer column. The ultrasound probe 2 supplies the aforementioned electrical signal to the transmission-reception processing unit 3. Through the above process, the transmission-reception processing unit 3 acquires a reception signal which can be used to generate the 2D image depicting the longitudinal cross-section of the carotid artery.

As illustrated in FIG. 2, the ultrasound probe 2 causes the transducer column to oscillate in the direction perpendicular to the arrangement direction, and acquires ultrasound echo signals for generating a plurality of 2D images that each depict a longitudinal cross-section of the carotid artery. More specifically, the ultrasound probe 2 acquires ultrasound echo signals for generating a plurality of 2D images that respectively depict longitudinal cross-sections of the carotid artery at each of a plurality of different positions of the transducers during oscillation. During the above, preferably an interval between subsequent acquisitions of 2D images that each depict a longitudinal cross-section of the carotid artery should be approximately equal to an interval between neighboring transducers arranged in the transducer column. For example, in a configuration in which an interval between neighboring transducers in the arrangement direction is 0.25 mm, supposing that the ultrasound diagnostic device has a frame rate of 20 frames per second, the transducer column is caused to oscillate at a speed in a range from 4 mm/s to 6 mm/s, and preferably at approximately 5 mm/s. Through the above, 2D images that each depict a longitudinal cross-section of the carotid artery are acquired at intervals in a range of 0.2 mm to 0.3 mm, and preferably at intervals of approximately 0.25 mm.

As explained above, the ultrasound probe 2 transmits an ultrasound beam while applied against the skin surface with the arrangement direction orientated along the longitudinal direction of the carotid artery. In accordance with oscillation of the transducer column, the ultrasound probe 2 acquires an ultrasound echo signal for each oscillation position, converts the ultrasound echo signal into an electrical signal, and supplies the electrical signal to the transmission-reception processing unit 3.

(Transmission-Reception Processing Unit 3)

The transmission-reception processing unit 3 performs transmission processing by generating a pulse or continuous electrical signal in order to cause the ultrasound probe 2 to transmit an ultrasound beam, and supplying the electrical signal to the ultrasound probe 2 as a transmission signal.

The transmission-reception processing unit 3 also performs reception processing by amplifying and A/D converting an electrical signal received from the ultrasound probe 2, thereby generating a reception signal. The reception signal may for example include a plurality of signals acquired in a direction along the transducer column and in a depth direction away from the transducer column, wherein each of the signals is a digital signal generated by A/D conversion of an electrical signal converted to from amplitude of an ultrasound echo signal.

Herein, a reception signal is generated for a longitudinal cross-section of each of a plurality of frames which are acquired at a plurality of oscillation positions in terms of the transverse direction of the carotid artery.

(Longitudinal Cross-sectional Image Generation Unit 4)

The longitudinal cross-sectional image generation unit 4 generates a longitudinal cross-sectional image of the carotid artery based on the reception signals for the longitudinal cross-sections of the plurality of frames. The longitudinal cross-sectional image is generated based on a reception signal for each of the transducers at a certain oscillation position of the transducers in the ultrasound probe 2, among the plurality of oscillation positions. The longitudinal cross-sectional image is an image signal in which coordinate conversion has mainly been applied to the reception signal in order to correspond to a Cartesian coordinate system.

In the first embodiment, a longitudinal cross-sectional image of the carotid artery is generated which corresponds to a central position in an oscillation range illustrated in FIG. 2. The aforementioned central position is a central one of the plurality of positions in the oscillation direction at which the transmission-reception processing unit 3 acquires a reception signal for a longitudinal cross-section. In a situation in which the transmission-reception processing unit 3 does not acquire a reception signal of a longitudinal cross-section at the central position, the longitudinal cross-sectional image generation unit 4 performs averaging or interpolation processing. In other words, among the reception signals of the longitudinal cross-sections which are respectively acquired at the plurality of different positions, reception signals respectively acquired at a plurality of positions in proximity to the central position are used in order to generate a longitudinal cross-sectional image of the carotid artery corresponding to the central position, by performing averaging or interpolation processing on the aforementioned reception signals. In an alternative configuration, longitudinal cross-sectional images of the carotid artery corresponding to a plurality of different positions in the oscillation direction may be generated.

(Longitudinal Cross-sectional Image Storage Unit 5)

The longitudinal cross-sectional image storage unit 5 stores therein a longitudinal cross-sectional image generated by the longitudinal cross-sectional image generation unit 4. In the configuration described above in which longitudinal cross-sectional images of the carotid artery corresponding to a plurality of positions in the oscillation direction are generated, the longitudinal cross-sectional image storage unit 5 stores the longitudinal cross-sectional images in an order in which the longitudinal cross-sectional images are acquired.

(Transverse Cross-sectional Image Generation Unit 6)

The transverse cross-sectional image generation unit 6 generates transverse cross-sectional images 300 of the carotid artery based on reception signals from the transmission-reception processing unit 3. The transverse cross-sectional image generation unit 6 generates each of the transverse cross-sectional images 300 from a reception signal of a certain transducer for each of the plurality of oscillation positions. The transverse cross-sectional image 300 is an image signal in which coordination conversion has been mainly applied to the reception signal in order to correspond to a Cartesian coordinate system. The processing described above is performed for each of the transducers in order to generate a transverse cross-sectional image 300 for each of a plurality of sequential frames in the arrangement direction, from a frame corresponding to a transducer at one end of the transducer column to a frame corresponding to a transducer at an opposite end of the transducer column.

(Transverse Cross-sectional Image Storage Unit 7)

Figure 3:
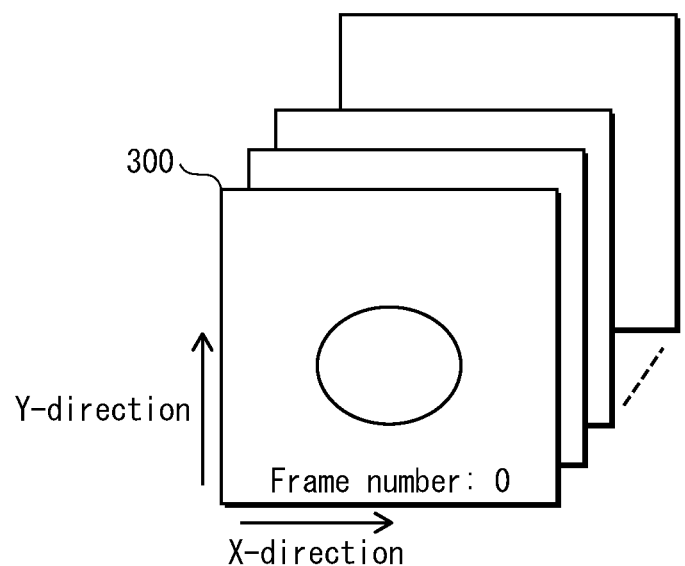
FIG. 3 illustrates, for the ultrasound diagnostic device 1 relating to the first embodiment, frames of an acquired reception signal which each include a transverse cross-sectional image 300.

FIG. 3 illustrates, for the ultrasound diagnostic device 1 relating to the first embodiment, frames of an acquired reception signal which each include a transverse cross-sectional image 300. The transverse cross-sectional image storage unit 7 stores therein the transverse cross-sectional image 300 of each of the frames, for example attaching a frame number to each of the transverse cross-sectional images 300 in order starting from a transverse cross-sectional image 300 generated using the transducer at the one end of the transducer column.

(Contour Extraction Unit 8)

The contour extraction unit 8 extracts contours of a vascular wall of the carotid artery depicted in the transverse cross-sectional image 300 of each of the frames stored in the transverse cross-sectional image storage unit 7. The contour extraction unit 8 for example performs contour extraction using a common image processing technique such as edge detection processing.

(3D Volume Data Storage Unit 9)

The 3D volume data storage unit 9 stores therein, for each of the frames, the contours in the transverse cross-sectional image 300 extracted by the contour extraction unit 8. Herein, a group of data extracted by performing contour extraction for the transverse cross-sectional image 300 of each of the plurality of frames is referred to as 3D volume data.

(Transverse Cross-sectional Image Selection Unit 10)

Figure 4:
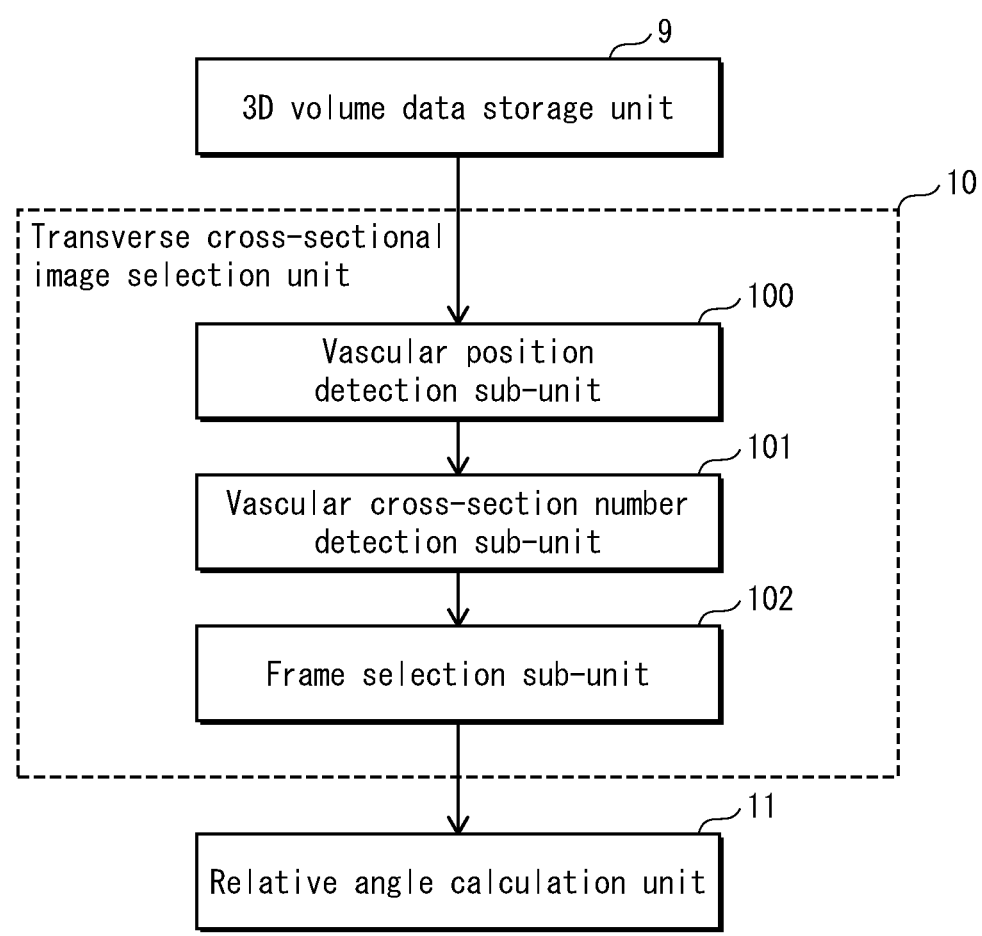
FIG. 4 is a block diagram illustrating functional configuration of a transverse cross-sectional image selection unit 10 in the ultrasound diagnostic device 1 relating to the first embodiment.

The transverse cross-sectional image selection unit 10 determines and selects a transverse cross-sectional image 300 of a frame corresponding to the bif 217 in terms of position. As illustrated in FIG. 4, the transverse cross-sectional image selection unit 10 includes a vascular position detection sub-unit 100, a vascular cross-section number detection sub-unit 101, and a frame selection sub-unit 102.

[Vascular Position Detection Sub-unit 100]

The vascular position detection sub-unit 100 determines, for each of the transverse cross-sectional images 300 to which the 3D volume data relates, coordinates at which a blood vessel is depicted in the transverse cross-sectional image 300. For example, the vascular position detection sub-unit 100 detects coordinates of contours corresponding to a transverse cross-section of a vascular wall. The vascular position detection sub-unit 100 also uses a position along the transducer column at which the corresponding transverse cross-sectional image 300 is acquired in order to determine a coordinate of each of the contours in terms of the longitudinal direction.

[Vascular Cross-section Number Detection Sub-unit 101]

The vascular cross-section number detection sub-unit 101 detects a number of cross-sections of the carotid artery which are depicted, which is indicated by a number of ring shaped contours in the 3D volume data.

[Frame Selection Sub-unit 102]

The frame selection sub-unit 102 determines and selects a frame for a transverse cross-sectional image 300 corresponding to the bif 217 in terms of position, from among transverse cross-sectional images 300 to which the 3D volume data relates. The bif 217 corresponds to a branching point from the bulb 214 to the ICA 215 and the ECA 216. The frame selection sub-unit 102 selects, as the frame for the transverse cross-sectional image 300 corresponding to the bif 217 in terms of position, a frame for a transverse cross-sectional image 300 for which the vascular cross-section number detection sub-unit 101 detects that a number of cross-sections of the carotid artery depicted therein has changed from one to two.

(Relative Angle Calculation Unit 11)

Figure 5:
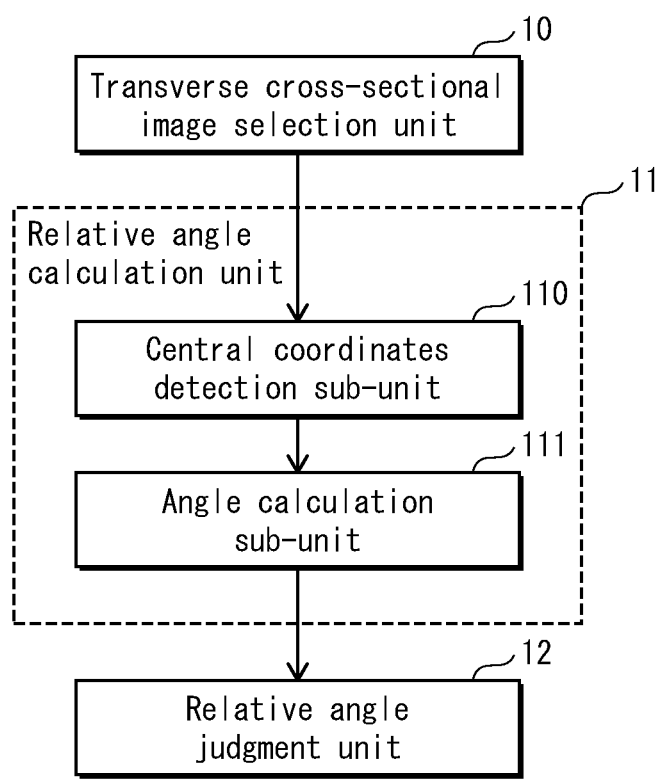
FIG. 5 is a block diagram illustrating functional configuration of a relative angle calculation unit 11 in the ultrasound diagnostic device 1 relating to the first embodiment.

As illustrated in FIG. 5, the relative angle calculation unit 11 includes a central coordinates detection sub-unit 110 and an angle calculation sub-unit 111.

[Central Coordinates Detection Sub-unit 110]

With respect to the transverse cross-sectional image 300 determined and selected by the transverse cross-sectional image selection unit 10, the central coordinates detection sub-unit 110 detects central coordinates of an ICA and an ECA depicted in the selected transverse cross-sectional image 300. In other words, the central coordinates detection sub-unit 110 detects central coordinates of a contour corresponding to the ICA and central coordinates of a contour corresponding to the ECA. The central coordinates can for example be detected using a commonly known method such as a method for calculating a centroid of a contour.

[Angle Calculation Sub-unit 111]

The angle calculation sub-unit 111 uses the central coordinates of the ICA 215 and the ECA 216 depicted in the transverse cross-sectional image 300, which are detected by the central coordinates detection sub-unit 110, in order to calculate a relative angle of the ICA 215 and the ECA 216, depicted in the transverse cross-sectional image 300, relative to the frame of the transverse cross-sectional image 300. The frame of the transverse cross-sectional image 300 is set using the ultrasound probe 2 as a reference. Calculation of the relative angle of the ICA 215 and the ECA 216 which are depicted in the transverse cross-sectional image 300, with respect to the frame of the transverse cross-sectional image 300, enables calculation of a relative angle of the ultrasound probe 2 in a plane parallel to a carotid artery transverse cross-section.

(Relative Angle Judgment Unit 12)

The relative angle judgment unit 12 performs a judgment as to whether the ultrasound probe 2 is positioned at a suitable angle in the plane parallel to the carotid artery transverse cross-section based on the relative angle calculated by the angle calculation sub-unit 111. During an initial examination using IMT measurement, the judgment is performed by comparing the relative angle calculated by the angle calculation sub-unit 111 and a reference angle that is a preset recommended angle. When the relative angle is within a predetermined range of the reference angle, the relative angle judgment unit 12 judges that the ultrasound probe 2 is positioned at a suitable angle. During subsequent examinations using IMT measurement, the judgment is performed by comparing the relative angle calculated by the angle calculation sub-unit 111 and a reference angle that is set as a relative angle of the ultrasound probe 2 which has been stored during a previous examination. When the relative angle is within a predetermined range of the reference angle, the relative angle judgment unit 12 judges that the ultrasound probe 2 is positioned at a suitable angle.

Consequently, in IMT measurement during an initial examination, an IMT measurement range can be determined at a predetermined position in a vascular wall in terms of a transverse cross-section of a carotid artery, regardless of variation in position or shape of the carotid artery arising between different subjects. Furthermore, in a series of periodic IMT measurements, IMT can be measured at the same position during each measurement regardless of variation in neck condition arising due to bending upwards, downwards, or sideways, thus enabling accurate diagnosis.

(Display Control Unit 15 and Display 16)

The display control unit 15 controls the display 16 to display the relative angle calculated by the angle calculation sub-unit 111 and results of the judgment performed by the relative angle judgment unit 12. When the relative angle is shifted relative to the reference angle, an operator of the ultrasound probe 2 adjusts angle of the ultrasound probe 2, while checking content displayed by the display 16, until the angle of the ultrasound probe 2 matches the reference angle.

Note that although the first embodiment has a configuration in which the display 16 displays the relative angle which is calculated and the results of the judgment, such a configuration is not a limitation. In other words, so long as the relative angle and the results of the judgment are notified to the operator, such information may alternatively be notified in a different manner. For example, the display 16 may display a difference between the reference angle and a current angle, or the aforementioned information may be notified to the operator through a sound, voice, warning light or the like, instead of through the display 16.

(ROI Determination Unit 13)

Upon the relative angle judgment unit 12 judging that the ultrasound probe 2 is positioned at a suitable angle, the ROI determination unit 13 receives a judgment signal from the relative angle judgment unit 12 and determines the ROI 211 in order to perform IMT measurement, by using a longitudinal cross-sectional image stored in the longitudinal cross-sectional image storage unit 5.

Figure 16:
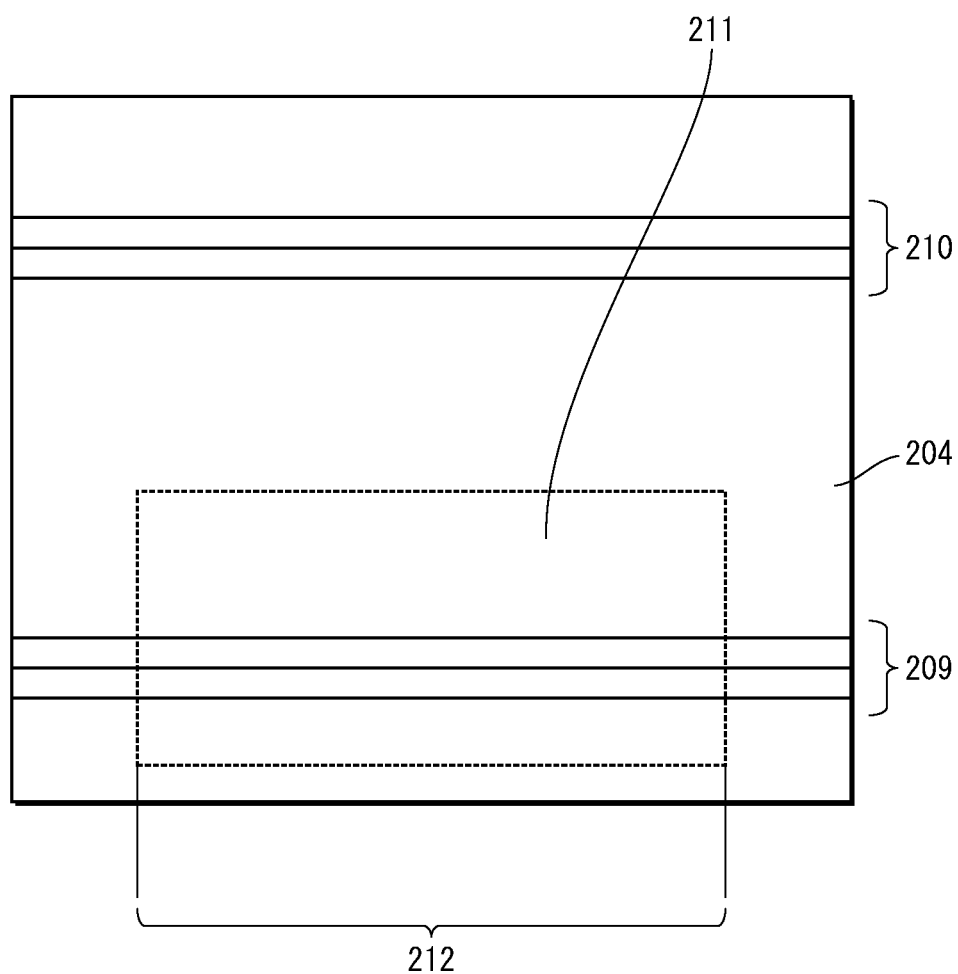
FIG. 16 is a schematic diagram illustrating a 2D image of the carotid artery along the longitudinal direction.
Figure 17:
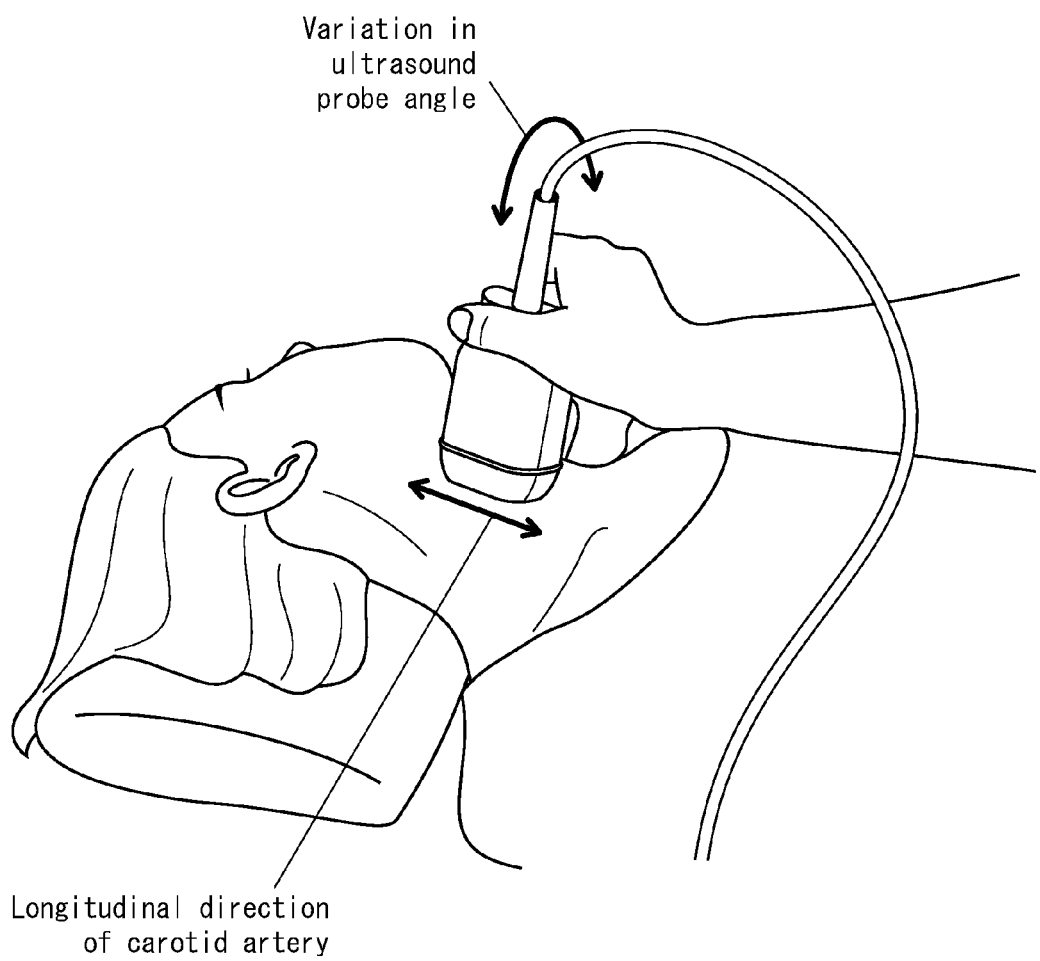
FIG. 17 is a schematic diagram illustrating a situation in which an ultrasound probe is applied against skin in proximity to a carotid artery of a subject when measuring a property of a vascular wall of the carotid artery using the ultrasound probe.

More specifically, the ROI determination unit 13 determines the ROI 211 based on position of the bif 217 detected by the transverse cross-sectional image selection unit 10. The ROI 211 defines a measurement range in which IMT measurement is performed. In other words, based on the position of the bif 217 detected by the transverse cross-sectional image selection unit 10, the ROI determination unit 13 selects a position in the longitudinal cross-sectional image stored in the longitudinal cross-sectional image storage unit 5 that corresponds to the preset IMT measurement range 212. For example, the ROI 211 may be determined based on the method disclosed in Non-Patent Literature 2, by detecting a lumen-intima interface and a media-adventitia interface depicted in the longitudinal cross-sectional image and determining the ROI 211 such as to span across a vascular wall as illustrated in FIG. 16.

Note that the present embodiment has a configuration in which ROI determination and IMT measurement are performed automatically upon judging that the ultrasound probe 2 is positioned at a suitable angle, but in an alternative configuration the operator may perform ROI determination manually upon seeing judgment results displayed on the display 16 which indicate that the ultrasound probe 2 is positioned at a suitable angle.

(IMT Measurement Unit 14)

The IMT measurement unit 14 measures IMT in the ROI 211 and calculates an IMT value which is for example a max. IMT or a mean IMT measured in the ROI 211. The display control unit 15 controls the display 16 to display the IMT value calculated by the IMT measurement unit 14.

In other words, the IMT measurement unit 14 performs IMT measurement in a range set by the ROI determination unit 13, in the longitudinal cross-sectional image stored in the longitudinal cross-sectional image storage unit 5. As explained further above, the vascular wall 201 is composed of the tunica intima 202, the tunica media 203, and the tunica adventitia 205 in respective order in an outwards direction, and IMT refers to thickness of the intima-media complex 206 composed of the tunica intima 202 and the tunica media 203. The IMT measurement unit 14 performs IMT measurement by detecting the intima-media complex 206 between the lumen 204 and the tunica adventitia 205 as depicted in the longitudinal cross-sectional image stored in the longitudinal cross-sectional image storage unit 5.

More specifically, the IMT measurement unit 14 detects a position of the lumen-intima interface 207 and a position of the media-adventitia interface 208 of the vascular wall in the ROI 211, based on signals corresponding to the ROI 211 among all signals corresponding to the longitudinal cross-sectional image stored in the longitudinal cross-sectional image storage unit 5. The IMT measurement unit 14 measures IMT by measuring a distance between the position of the lumen-intima interface 207 and the position of the media-adventitia interface 208.

Detection of the respective positions of the lumen-intima interface 207 and the media-adventitia interface 208 in order to perform IMT measurement, can be performed based on a commonly known method. For example, the IMT measurement unit 14 may detect the respective positions of the lumen-intima interface 207 and the media-adventitia interface 208 based on a signal intensity waveform corresponding to the longitudinal cross-sectional image using a method disclosed in International Publication No. WO2007/108359.

Results of the aforementioned IMT measurement are displayed on the display 16. Note that a 3D image may be constructed from the contours in the transverse cross-sectional image 300 of each frame by connecting the contours for all of the frames in an order corresponding to order of the frames. The 3D image may be displayed along with the IMT measurement range 212 in which IMT is measured. Through the above, information is displayed in a form which can be easily understood by the operator, improving usability.

<Operation>

Figure 6:
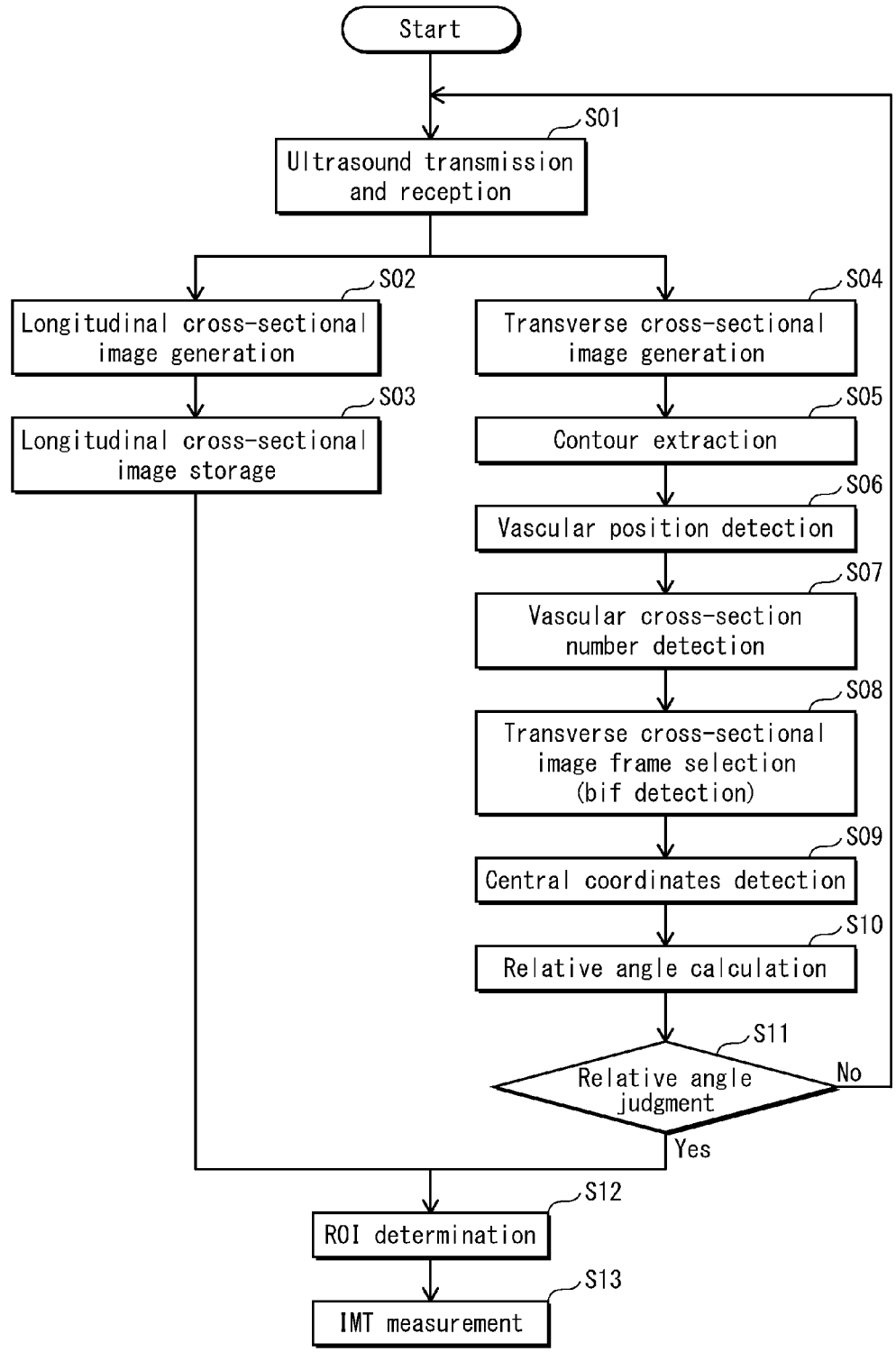
FIG. 6 is a flowchart illustrating operation of the ultrasound diagnostic device 1 relating to the first embodiment.

The following explains operation of the ultrasound diagnostic device 1, configuration of which is described above. FIG. 6 is a flowchart illustrating operation of the ultrasound diagnostic device 1 relating to the first embodiment.

(Step 1 (S01))

In Step 1 (S01) the transmission-reception processing unit 3 performs transmission processing and reception processing of ultrasound with the ultrasound probe 2 applied again skin surface of the nape of the neck such that the arrangement direction of the transducers is orientated along the longitudinal direction of the carotid artery. Through the above, the transmission-reception processing unit 3 generates a reception signal based on an electrical signal from the ultrasound probe 2. The transmission-reception processing unit 3 acquires an ultrasound echo signal for each of a plurality of oscillation positions in terms of the transverse direction of the carotid artery by causing oscillation, in the transverse direction, of the transducer column of the ultrasound probe 2. Based on the ultrasound echo signals which are for longitudinal cross-sections of a plurality of frames, the transmission-reception processing unit 3 generates a reception signal for the longitudinal cross-section of each of the frames.

(Step 2 (S02))

In Step 2 (S02), based on the reception signals acquired in Step 1 (S01) for the longitudinal cross-sections of the plurality of frames, the longitudinal cross-sectional image generation unit 4 generates one or more longitudinal cross-sectional images. The longitudinal cross-sectional image generation unit 4 generates each of the longitudinal cross-sectional images based on reception signals for each of the transducers of the ultrasound probe 2 at a certain oscillation position among the plurality of oscillation positions of the transducer column. In the present configuration, the longitudinal cross-sectional image generation unit 4 generates a longitudinal cross-sectional image of the carotid artery which corresponds to the central position in the oscillation range of the transducer column.

(Step 3 (S03))

In Step 3 (S03) the controller 400 stores the longitudinal cross-sectional image, which is generated by the longitudinal cross-sectional image generation unit 4 in Step 1 (S01), in the longitudinal cross-sectional image storage unit 5.

(Step 4 (S04))

In Step 4 (S04) the transverse cross-sectional image generation unit 6 generates a transverse cross-sectional image 300 using a reception signal for a certain transducer at each of the oscillation positions from among the reception signals generated in Step 1 (S01). The above processing is performed with respect to each of the transducers, thus generating a transverse cross-sectional image 300 for each of a plurality of successive frames ranging from a frame corresponding to a transducer located at one end of the transducer column to a frame corresponding to a transducer located at an opposite end of the transducer column. As illustrated in FIG. 3, a frame number is attached to the transverse cross-sectional image 300 of each of the frames in order starting from a transverse cross-sectional image 300 generated through the transducer located at the one end of the transducer column, and each of the transverse cross-sectional images 300 is stored in the transverse cross-sectional image storage unit 7.

(Step 5 (S05))

In Step 5 (S05) the contour extraction unit 8 extracts contours of the carotid artery depicted in each of the transverse cross-sectional images 300 stored in the transverse cross-sectional image storage unit 7 for each of the frames. The contour extraction unit 8 for example extracts the contours using a commonly known image processing technique such as edge detection processing. Each of the transverse cross-sectional images 300 on which contour extraction has been performed is stored as 3D volume data in the 3D volume data storage unit 9.

(Step 6 (S06))

In Step 6 (S06), the vascular position detection sub-unit 100 detects, for each of the transverse cross-sectional images 300 stored in the 3D volume data storage unit 9, coordinates of a blood vessel depicted therein. For example, the vascular position detection sub-unit 100 detects coordinates of contours for a vascular wall in a transverse cross-section through image scanning, wherein the contours identify position of the vascular wall within the frame. The vascular position detection sub-unit 100 also determines a coordinate of each of the contours in terms of the longitudinal direction. The coordinate in the longitudinal direction is determined by position in the transducer column of a transducer through which the transverse cross-sectional image 300 is acquired.
(Step 7 (S07))

In Step 7 (S07) the vascular cross-section number detection sub-unit 101 detects, for each of the frames, a number of vascular cross-sections depicted in the transverse cross-sectional image 300 of the frame. As a rule, the number of vascular cross-sections is one when detected for a frame which has been acquired with respect to the CCA and the number of vascular cross-sections is two when detected for a frame which has be acquired with respect to the ICA and the ECA.
(Step 8 (S08))

In Step 8 (S08) the frame selection sub-unit 102 detects the bif 217 based on the number of vascular cross-sections for each of the frames detected by the vascular cross-section number detection sub-unit 101, and selects a frame for which the transverse cross-sectional image 300 depicts the bif 217. As explained above, the bif 217 is a point at which branching occurs from the bulb 214 to the ICA 215 and the ECA 216. Therefore, the frame selection sub-unit 102 is able to select the frame for which the transverse cross-sectional image 300 depicts the bif 217 by, in terms of an order of frames from the CCA 213 towards the ICA 215 and the ECA 216, selecting a first frame for which the transverse cross-sectional image 300 depicts two vascular cross-sections instead of one.

Figure 7A:
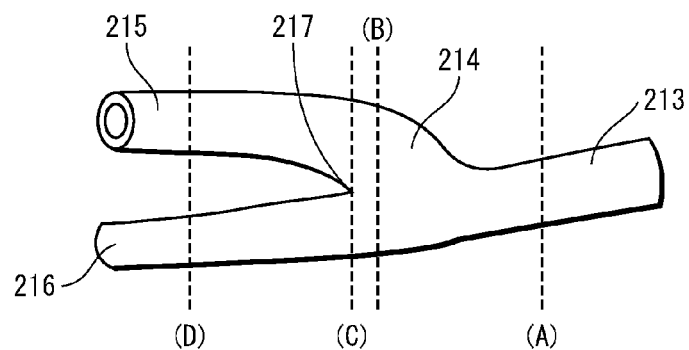
FIG. 7A is a schematic diagram illustrating different positions along an extension direction of a carotid artery.
Figure 7B:
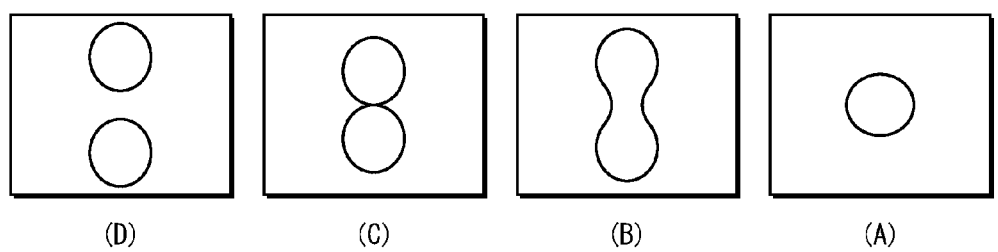
FIG. 7B is a schematic diagram illustrating 2D cross-sectional images of the carotid artery that are respectively acquired at positions (A) to (D) illustrated in FIG. 7A.

FIG. 7A is a schematic diagram illustrating a plurality of different positions along an extension direction of the carotid artery. FIG. 7B is a schematic diagram illustrating 2D cross-sectional images of the carotid artery acquired at positions (A) to (D) illustrated in FIG. 7A. Among the plurality of transverse cross-sectional images 300 of the carotid artery, in FIG. 7B image (A) illustrates a transverse cross-sectional image 300 acquired of the CCA 213, image (B) illustrates a transverse cross-sectional image 300 acquired of the bulb 214 in proximity to the bif 217, image (C) illustrates a transverse cross-sectional image 300 acquired of the bif 217, and image (D) illustrates a transverse cross-sectional image 300 acquired of the ICA 215 and the ECA 216.

As explained above, the bif 217 is a point at which branching occurs from the CCA 213 and the bulb 214, to the ICA 215 and the ECA 216. Consequently, position of the bif 217 can be determined as a position corresponding to a transverse cross-sectional image 300 in which contours of the ICA 215 and the ECA 216 are in contact, thus appearing as a single contour as illustrated in image (C) in FIG. 7B. Therefore, the frame of the transverse cross-sectional image 300 corresponding to image (C) in FIG. 7B is selected as the frame of the transverse cross-sectional image 300 which depicts the bif 217.

Note that although the first embodiment has a configuration in which the frame selection sub-unit 102 selects a frame for a position corresponding to the bif 217, such a configuration is not a limitation. For example, in an alternative configuration a frame may be selected which is a certain number of frames in a direction towards the ICA 215 and the ECA 216 from the bif 217.

Further alternatively, a frame may be selected for a position in proximity to the bif 217 which is in a direction towards the bulb 214 from the bif 217, and thus in which a cross-section of the ICA 215 and a cross-section of the ECA 216 are depicted as partially connected cross-sections such as illustrated in image (B) in FIG. 7B. In other words, a frame should be selected from which two sets of central coordinates can be acquired by the relative angle calculation unit 11 in Step 9 (S09), either of two cross-sections respectively of the ICA 215 and the ECA 216, or of a single cross-section which is equivalent to the two cross-sections in terms of being able to acquire the two sets of central coordinates.

Consequently, when the frame selection sub-unit 102 selects a frame in which two transverse cross-sections are depicted which are respectively of the ICA 215 and the ECA 216, the frame selection sub-unit 102 is not limited to selecting a frame in which the cross-section of the ICA 215 and the cross-section of the ECA 216 are depicted as two independent cross-sections, but can also select a frame in which the cross-section of the ICA 215 and the cross-section of the ECA 216 are connected, so long as central coordinates of each of the aforementioned cross-sections can be determined.
(Step 9 (S09))

Figure 8:
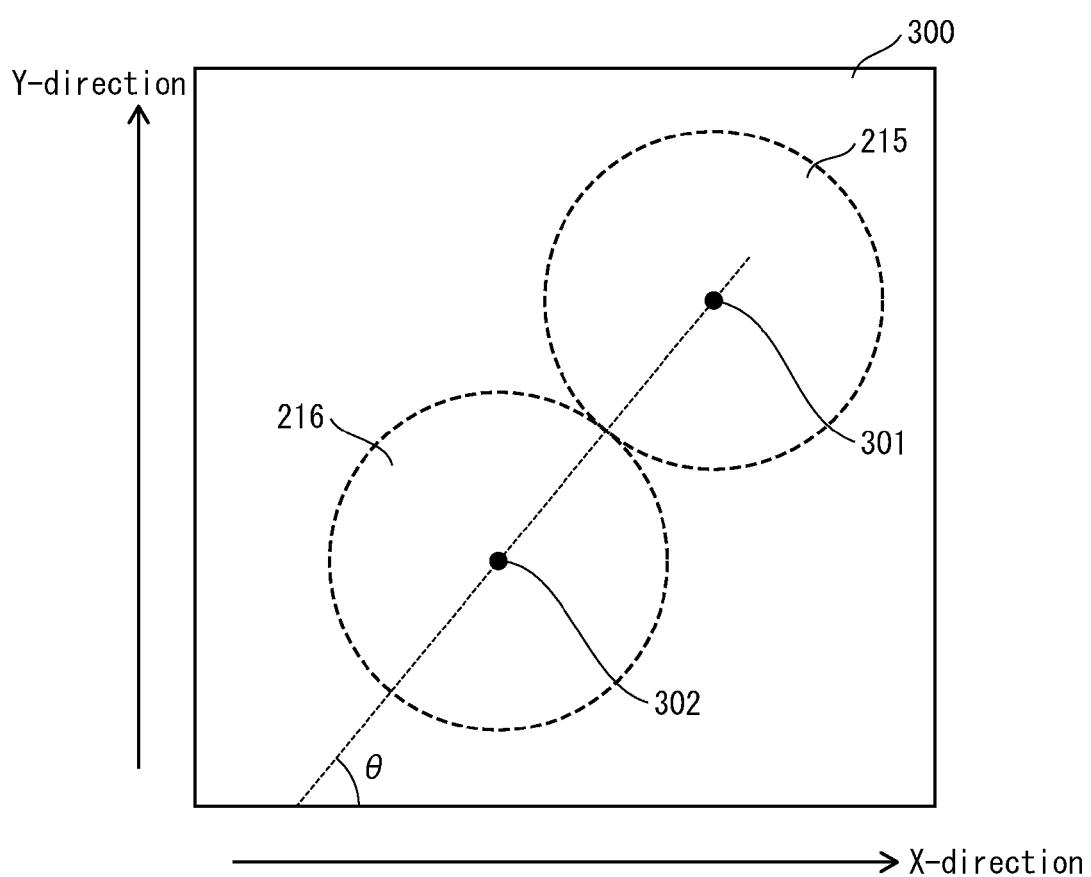
FIG. 8 is a cross-sectional schematic diagram illustrating, for the ultrasound diagnostic device 1 relating to the first embodiment, one example of a method for calculating a relative angle of the ultrasound probe with respect to the carotid artery in a plane parallel to a carotid artery transverse cross-section.

In Step 9 (S09) the relative angle calculation unit 11 detects two sets of central coordinates in a transverse cross-sectional image 300 for the frame selected by the frame selection sub-unit 102. FIG. 8 is a cross-sectional schematic diagram illustrating one example of a method used in the ultrasound diagnostic device 1 relating to the first embodiment in order to calculate a relative angle of the ultrasound probe with respect to the carotid artery in a plane parallel to a carotid artery transverse cross-section. FIG. 8 illustrates an example of the frame selected by the frame selection sub-unit 102 for which the transverse cross-sectional image 300 depicts the bif 217. A Y-axis in FIG. 8 corresponds to a depth direction in which ultrasound is transmitted to and received from the carotid artery by the ultrasound probe 2 when the transducer column is at the central position in the oscillation range. An X-axis in FIG. 8 corresponds to a direction which is perpendicular to the Y-axis.

As illustrated in FIG. 8, in Step 9 (S09) the central coordinates detection sub-unit 110 detects central coordinates 301 of the ICA 215 depicted in the transverse cross-sectional image 300 and central coordinates 302 of the ECA 216 depicted in the transverse cross-sectional image 300, in accordance with the X-axis and the Y-axis. Note that the central coordinates may for example be coordinates of a centroid of a corresponding contour (i.e., coordinates which are averaged values of all coordinates of the contour), or may be coordinates midway between maximum and minimum coordinates of the contour in terms of the X-axis and the Y-axis.
(Step 10 (S10))

In Step 10 (S10) the angle calculation sub-unit 111 calculates a relative angle of the ultrasound probe 2 with respect to the carotid artery. As illustrated in FIG. 8, the angle calculation sub-unit 111 calculates an angle θ between the X-axis and a straight line passing through the central coordinates 301 and 302. Through the above, an angle at which the ultrasound probe 2 is positioned can be calculated using, as references, the Y-axis along which ultrasound is transmitted and received by the ultrasound probe 2 when the transducer column is at the central position in oscillation range, and the X-axis perpendicular to the Y-axis. In other words, a relative angle of the ultrasound probe 2 can be calculated in a plane parallel to a carotid artery transverse cross-section.
(Step 11 (S11))

In Step 11 (S11) the relative angle judgment unit 12 performs a judgment as to whether the relative angle calculated in Step 10 (S10) is a suitable angle. The judgment is performed as explained below.

In a situation in which IMT measurement is being performed during an initial examination of a subject, the relative angle judgment unit 12 compares the relative angle calculated by the angle calculation sub-unit 111 in Step 10 (S10) with a reference angle which is a preset recommended angle. The relative angle judgment unit 12 judges whether the relative angle is within a predetermined range of the reference angle. When the relative angle is within the predetermined range of the reference angle, the relative angle judgment unit 12 judges that the ultrasound probe 2 is positioned at a suitable angle.

In a situation in which IMT measurement is being performed during a second examination of a subject, or any examination subsequent thereto, the relative angle judgment unit 12 compares the relative angle calculated by the angle calculation sub-unit 111 in Step 10 (S10) with a reference angle which is a relative angle of the ultrasound probe 2 that has been stored during a past IMT measurement. The relative angle judgment unit 12 judges whether the relative angle is within a predetermined range of the reference angle. When the relative angle is within the predetermined range of the reference angle, the relative angle judgment unit 12 judges that the ultrasound probe 2 is positioned at a similar angle to during the past IMT measurement.

The display control unit 15 controls the display 16 to display results of the judgment described above. In other words, an actual measured value of the relative angle of the ultrasound 2 in the plane parallel to the carotid artery transverse cross-section and the results of the judgment by the relative angle judgment unit 12 can be checked by the operator in real-time using the display 16, while the ultrasound probe 2 is applied against the surface of the nape of the neck.

When the ultrasound probe 2 is not positioned as a suitable angle, operation is repeated from Step 1 (S01) and the operator adjusts angle of the ultrasound probe 2 while checking the display 16 in order to position the ultrasound probe 2 at a suitable angle. Steps 1 (S01) to 11 (S11) are repeated until the ultrasound probe 2 is positioned at a suitable angle.

Step 12 (S12) is performed once the ultrasound probe 2 is positioned at a suitable angle. Transition to Step 12 (S12) is performed automatically by the controller 400, but alternatively the operator may check the display 16 and perform transition to Step 12 (S12) manually.

(Step 12 (S12))

Figure 12:
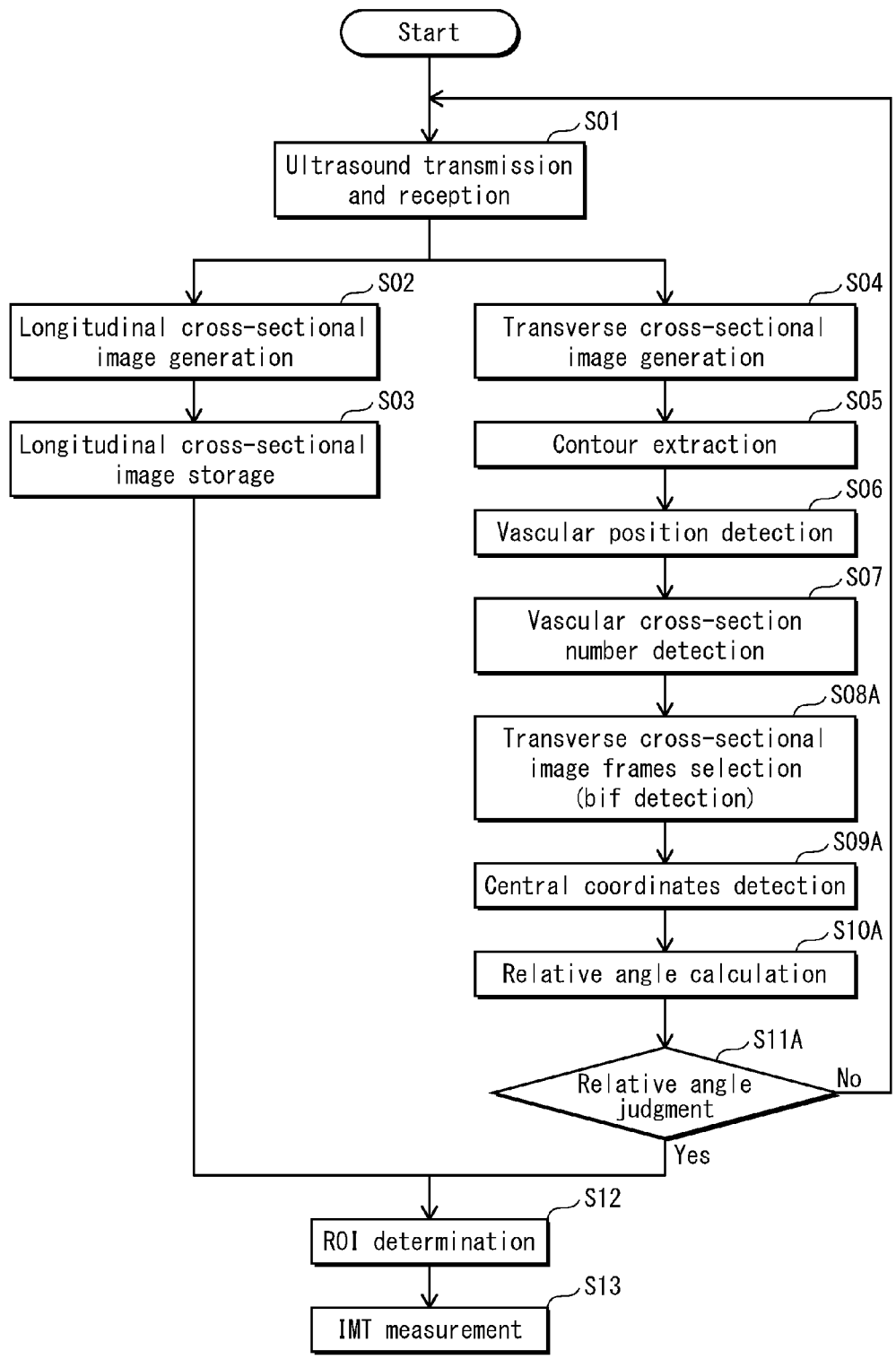
FIG. 12 is a flowchart illustrating operation of the ultrasound diagnostic device 1A relating to the second embodiment.

Once the ultrasound probe 2 has been positioned at a suitable angle in Step 11 (S11), in Step 12 (S12) the ROI determination unit 13 sets the IMT measurement range 212 in accordance with the bif 217 detected in Step 8 (S08). In other words, the ROI determination unit 13 selects a predetermined position corresponding to the IMT measurement range 212 in the longitudinal cross-sectional image stored in the longitudinal cross-sectional image storage unit 5, in accordance with the bif 217, and thus determines the ROI 211 which defines a range in which IMT measurement is performed. For example, a lumen-intima interface and a media-adventitia interface depicted in the longitudinal cross-sectional image may be detected, and the ROI 211 may be determined so as to span across the vascular wall as illustrated in FIG. 12, based on the method disclosed in Non-Patent Literature 2.

The present embodiment has a configuration in which, upon judging that the ultrasound probe 2 is positioned at a suitable angle in Step 11(S11), an ROI is automatically determined in Step 12 (S12) and IMT measurement is performed. However, in an alternative configuration the operator may manually determine an ROI upon seeing judgment results displayed on the display 16 which indicate that the ultrasound probe 2 is positioned at a suitable angle. (Step 13 (S13))

In Step 13 (S13) the IMT measurement unit 14 performs IMT measurement using the longitudinal cross-sectional image stored in the longitudinal cross-sectional image storage unit 5 in Step 3 (S03). More specifically, the IMT measurement unit 14 performs IMT measurement in a range in the aforementioned longitudinal cross-sectional image which is determined by the ROI determination unit 13. The IMT measurement unit 14 for example determines an IMT value using measurement results for max. IMT, mean IMT, or the like in the IMT measurement range 212, thus completing IMT measurement.

<Effects>

Through the configuration described above, the ultrasound diagnostic device and the method for controlling an ultrasound diagnostic device relating to the present embodiment calculate a relative angle of the ultrasound probe 2 with respect to the carotid artery based on a transverse cross-sectional image 300 which depicts two transverse cross-sections respectively of the ICA 215 and the ECA 216. Judgment is also performed as to whether the relative angle which is calculated is a suitable angle, and results of the judgment are notified to the operator. IMT measurement is performed once the relative angle which is calculated is judged to be a suitable angle.

Through the above, in IMT measurement during an initial examination, an IMT measurement range can be set at a predetermined position in a vascular wall in a transverse cross-section of a carotid artery, regardless of variation in position or shape of the carotid artery between different subjects. Furthermore, during a series of periodic IMT measurements, IMT can be measured at the same position during each measurement, regardless of variation in neck condition due to upwards, downwards, or sideways bending, enabling accurate diagnosis.

Furthermore, the operator can be notified of a current angle of the ultrasound probe in a plane parallel to a carotid artery transverse cross-section and a suitable angle at which the ultrasound probe should be positioned, through display of the current angle and the suitable angle on the display. Therefore, the operator can adjust the ultrasound probe to an appropriate angle in real-time based on the display which functions as a notification unit. Conventionally, determination of an IMT measurement range of a vascular wall in a carotid artery transverse cross-section is difficult for an operator who does not possess a high degree of procedural skill, and a significant amount of examination time is necessary in order to ensure accurate measurement. In contrast, the present embodiment enables real-time adjustment of the ultrasound probe to a suitable angle, thus enabling simple IMT measurement.

<<Second Embodiment>>

The ultrasound diagnostic device 1 relating to the first embodiment has a configuration in which the transverse cross-sectional image selection unit 10 selects a transverse cross-sectional image 300 of a frame corresponding to the bifurcation of the common carotid artery, and the relative angle calculation unit 11 calculates a relative angle of the ultrasound probe in a plane parallel to a carotid artery transverse cross-section based on the ICA 215 and the ECA 216. In order to enable calculation of a relative angle of the ultrasound probe with greater accuracy, an ultrasound diagnostic device 1A relating to a second embodiment calculates the aforementioned relative angle based on a transverse cross-sectional image 300 that depicts a cross-section of the ICA 215 and a cross-section of the ECA 216, and also based on a transverse cross-sectional image 300 that depicts a cross-section of the bulb 214 or a cross-section of the CCA 213.

<Configuration>
(General Configuration)

Figure 9:
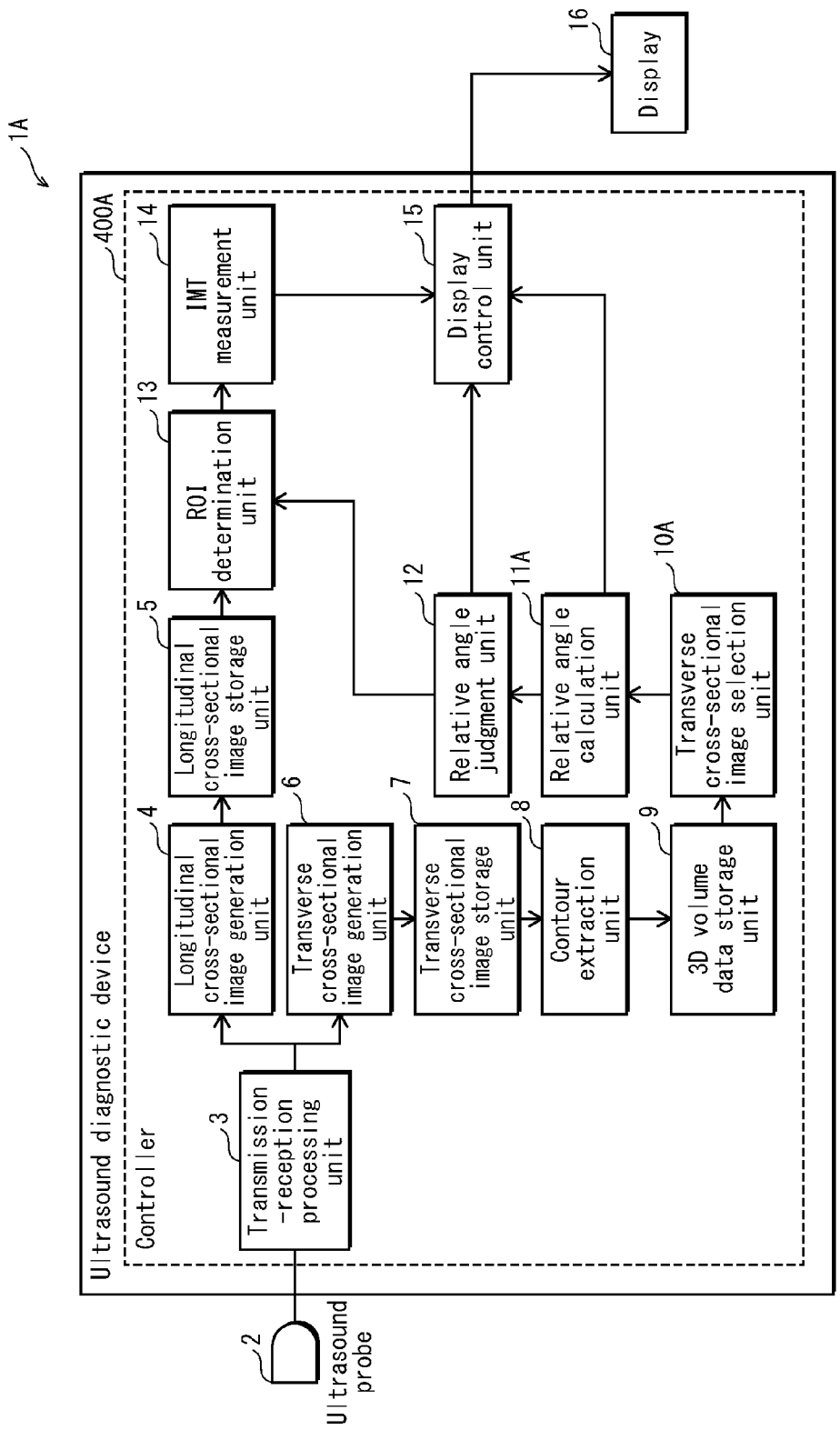
FIG. 9 is a block diagram illustrating functional configuration of an ultrasound diagnostic device 1A relating to a second embodiment.

The following explains configuration of the ultrasound diagnostic device 1A relating to the second embodiment. FIG. 9 is a block diagram illustrating functional configuration of the ultrasound diagnostic device 1A. As illustrated in FIG. 9, the ultrasound diagnostic device 1A relating to the second embodiment differs from the ultrasound diagnostic device 1 relating to the first embodiment in terms of configuration of a transverse cross-sectional image selection unit 10A and a relative angle calculation unit 11A included in a controller 400A. Other configuration elements are the same as illustrated in FIG. 1 and explanation of such configuration elements is omitted. Detailed explanation of configuration of the ultrasound diagnostic device 1A relating to the second embodiment is provided below with reference to FIG. 9.

(Transverse Cross-sectional Image Selection Unit 10A)

Figure 10:
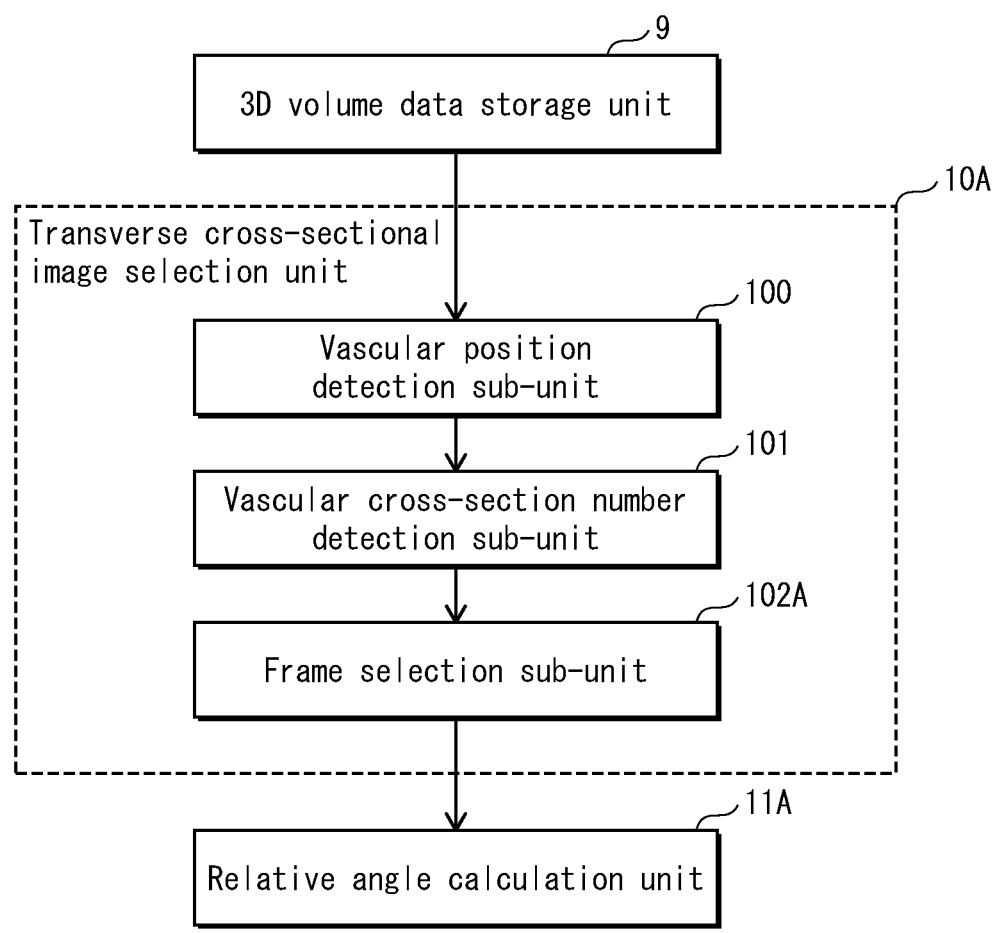
FIG. 10 is a block diagram illustrating functional configuration of a transverse cross-sectional image selection unit 10A in the ultrasound diagnostic device 1A relating to the second embodiment.

FIG. 10 is a block diagram illustrating functional configuration of the transverse cross-sectional image selection unit 10A in the ultrasound diagnostic device 1A relating to the second embodiment. As illustrated in FIG. 10, the transverse cross-sectional image selection unit 10A includes a vascular position detection sub-unit 100, a vascular cross-section number detection sub-unit 101, and a frame selection sub-unit 102A in the same way as in the first embodiment. The vascular position detection sub-unit 100 and the vascular cross-section number detection sub-unit 101 are the same as in the first embodiment and explanation thereof is omitted. The frame selection sub-unit 102A selects two frames from the 3D volume data. In the same way as in the first embodiment, one of the frames corresponds to the bif 217 in terms of position. The other frame is a frame which is a predetermined number of frames from the bif 217 in a direction towards the CCA 213.

(Relative Angle Calculation Unit 11A)

Figure 11:
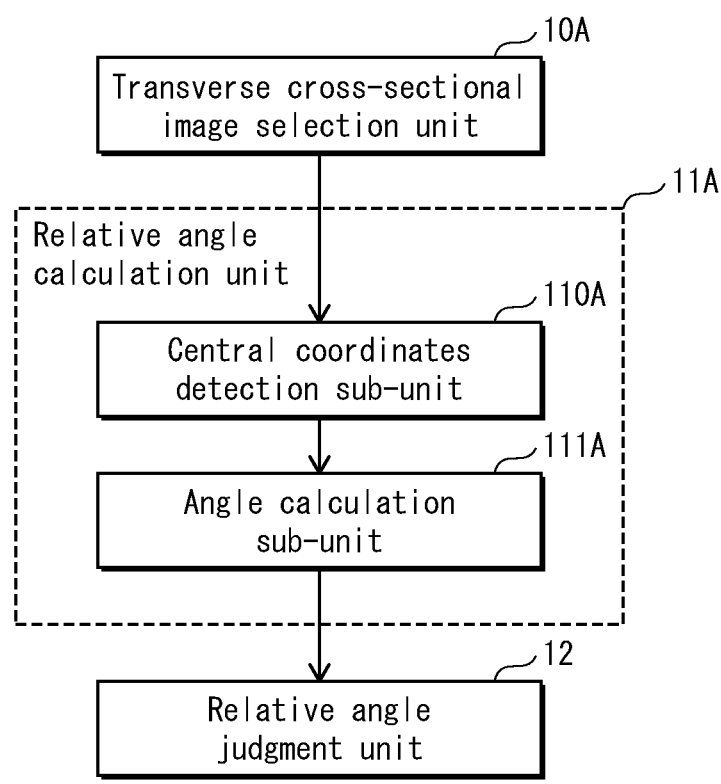
FIG. 11 is a block diagram illustrating functional configuration of a relative angle calculation unit 11A in the ultrasound diagnostic device 1A relating to the second embodiment.

FIG. 11 is a block diagram illustrating functional configuration of the relative angle calculation unit 11A in the ultrasound diagnostic device 1A relating to the second embodiment. The relative angle calculation unit 11A includes a central coordinates detection sub-unit 110A and an angle calculation sub-unit 111A in the same way as in the first embodiment.

The central coordinates detection sub-unit 110A detects central coordinates of contours in respective transverse cross-sectional images 300 of the two frames selected by the transverse cross-sectional image selection unit 10A. In other words, the central coordinates detection sub-unit 110A detects central coordinates of a contour of the ICA 215 and a contour of the ECA 216 depicted in a transverse cross-sectional image 300 of one of the frames, and detects central coordinates of a contour of the CCA 213 or a contour of the bulb 214 depicted in a transverse cross-sectional image 300 of the other frame.

The angle calculation sub-unit 111A calculates a relative angle of the ultrasound probe 2 with respect to the carotid artery in a plane parallel to a carotid artery transverse cross-section, based on three sets of central coordinates which are detected by the central coordinates detection sub-unit 110A as described above.

<Operation>

The following explains operation of the ultrasound diagnostic device 1A relating to the second embodiment, configuration of which is described above. FIG. 12 is a flowchart illustrating operation of the ultrasound diagnostic device 1A.

(Steps 1 (S01) to 7 (S07))

Steps from Step 1 (S01), in which transmission processing and reception processing of ultrasound are performed, to Step 7 (S07), in which a number of vascular cross-sections which are depicted is detected for each frame for which a transverse cross-sectional image 300 is generated, are the same as for the ultrasound diagnostic device 1 relating to the first embodiment. Therefore, explanation of Steps 1 (S01) to 7 (S07) is omitted.

(Step 8A (S08A))

In Step 8A (S08A) the frame selection sub-unit 102A detects the bif 217 based on the number of vascular cross-sections detected for each of the frames by the vascular cross-section number detection sub-unit 101, and selects two frames to be used in calculation of the relative angle of the ultrasound probe 2 with respect to the carotid artery.

The frame selection sub-unit 102A first detects the bif 217 in the same way as described in the first embodiment. Next, the frame selection sub-unit 102A selects a frame which is a predetermined number of frames from a frame corresponding to the bif 217 (herein, referred to as a reference frame) in a direction towards the ICA 215 and the ECA 216 (herein, referred to as a peripheral direction). The frame selection sub-unit 102A also selects a frame which is a predetermined number of frames from the reference frame in a direction towards the CCA 213 (herein, referred to as a central direction).

During selection of the two frames described above, by selecting the frame which is in the peripheral direction, the frame selection sub-unit 102A selects a frame depicting a cross-section of the ICA 215 and a cross-section of the ECA 216 in the same way as in the first embodiment. Also, by selecting the frame which is in the central direction, the frame selection sub-unit 102A selects a frame depicting a cross-section of the CCA 213, or alternatively a cross-section of the bulb 214.

(Step 9A (S09A))

In Step 9A (S09A) the relative angle calculation unit 11A detects central coordinates of the respective cross-sections of the ICA 215, the ECA 216, and the CCA 213 depicted in the two frames selected by the frame selection sub-unit 102A. The central coordinates are detected using the same method as described in the first embodiment.

(Step 10A (S10A))

In Step 10A (S10A) the angle calculation sub-unit 111A calculates a relative angle of the ultrasound probe with respect to the carotid artery in a plane parallel to a carotid artery transverse cross-section, using the central coordinates detected in Step 9A (S09A) of the respective cross-sections of the ICA 215, the ECA 216, and the CCA 213. The following explains, with reference to the drawings, one example of a method for calculating the relative angle of the ultrasound probe 2.

Figure 13:
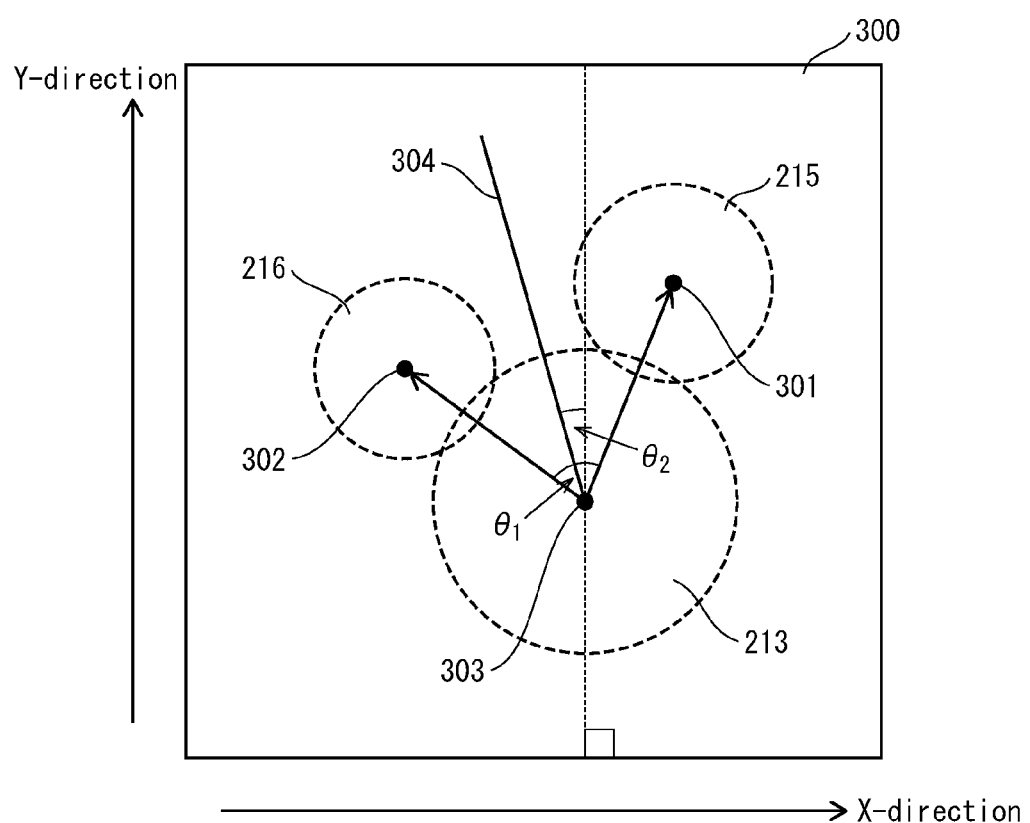
FIG. 13 is a cross-sectional schematic diagram illustrating, for the ultrasound diagnostic device 1A relating to the second embodiment, one example of a method for calculating a relative angle of the ultrasound probe with respect to the carotid artery in a plane parallel to a carotid artery transverse cross-section.
Figure 14:
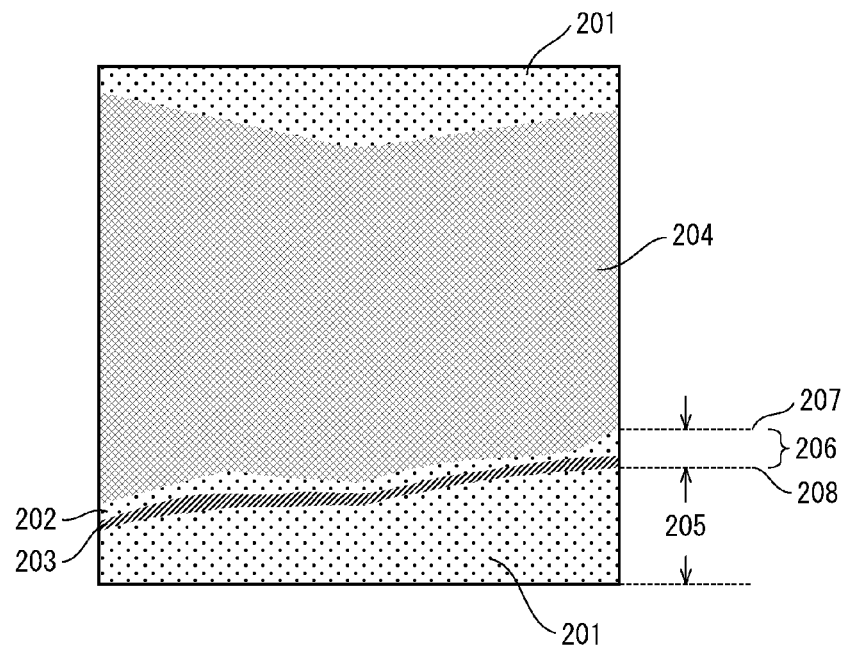
FIG. 14 is a cross-sectional diagram illustrating a cross-section of the carotid artery in a longitudinal direction along the carotid artery.

FIG. 13 is a cross-sectional schematic diagram illustrating, for the ultrasound diagnostic device 1A relating to the second embodiment, one method for calculating the relative angle of the ultrasound probe 2 with respect to the carotid artery in the plane parallel to the carotid artery transverse cross-section. FIG. 13 illustrates positions at which the ICA 215, the ECA 216, and the CCA 213 are depicted in the two frames selected by the frame selection sub-unit 102A, in terms of coordinates along an X-axis and a Y-axis. Note that the respective cross-sections of the ICA 215, the ECA 216, and the CCA 213 are illustrated in the same plane in FIG. 13 in order to facilitate understanding. In the same way as in FIG. 8, the Y-axis corresponds to the depth direction along which ultrasound is transmitted and received by the ultrasound probe 2 when the transducer column is at the central position in the oscillation range, and the X-axis corresponds to a direction perpendicular to the Y-axis.

In Step 10A (S10A) the angle calculation sub-unit 111A first calculates an angle $\theta_1$ formed between a straight line joining central coordinates 303 of the CCA 213 and central coordinates 301 of the ICA 215, and a straight line joining central coordinates 303 of the CCA 213 and central coordinates 302 of the ECA 216. Next, the angle calculation sub-unit 111A sets a straight line that passes through the central coordinates 303 of the CCA 213 and that divides the angle $\theta_1$ into two equal segments as a reference line 304. The angle calculation sub-unit 111A subsequently calculates an angle $\theta_2$ formed between the reference line 304 and the Y-axis. The angle $\theta_2$ is used as the relative angle of the ultrasound probe 2 in the plane parallel to the carotid artery transverse cross-section. The method described above enables calculation of an angle at which the ultrasound probe 2 is positioned using, as references, the Y-axis along which ultrasound is transmitted and received the ultrasound probe 2 when the transducer column is at the central position in the oscillation range, and the X-axis which is perpendicular to the Y-axis. In other words, the method described above enables calculation of the relative angle of the ultrasound probe 2 in the plane parallel to the carotid artery transverse cross-section.

As described above, in the present embodiment relative angle of the ultrasound probe in the plane parallel to the carotid artery transverse cross-section is calculated based on central coordinates of respective cross-sections of the ICA 215, the ECA 216, and the CCA 213, which are detected in transverse cross-sectional images 300 of a plurality of frames which are separated from each other by a predetermined number of frames. Through the above, relative angle of the ultrasound probe can be calculated with greater accuracy than in the configuration described in the first embodiment, in which relative angle of the ultrasound probe is calculated using only a single frame for which the transverse cross-sectional image 300 depicts the bif 217.
(Step 11A (S11A))

In Step 11A (S11A) the relative angle judgment unit 12 performs a judgment as to whether the relative angle calculated in Step 10A (S10A) is a suitable angle, by using a preset angle or a relative angle of the ultrasound probe 2 stored during a past measurement as a reference angle. The above judgment is performed using the same method as in the ultrasound diagnostic device 1 relating to the first embodiment and explanation thereof is omitted. The present embodiment differs to the first embodiment in terms that in Step 11A (S11A), the reference angle is a relative angle of the ultrasound probe in the plane parallel to the carotid artery transverse cross-section which is calculated based on three sets of central coordinates of respective cross-sections of the ICA 215, the ECA 216, and the CCA 213.

The display control unit 15 controls the display 16 to display results of the judgment described above. When the ultrasound probe 2 is positioned at a suitable angle, operation proceeds to Step 12 (S12). On the other hand, when the ultrasound probe 2 is not positioned at a suitable angle, operation is repeated from Step 1 (S01) and the operator adjusts angle of the ultrasound probe 2, based on the judgment results displayed on the display 16, in order to position the ultrasound probe 2 at a suitable angle.
(Steps 12 (S12) and 13 (S13))

When the ultrasound probe 2 is positioned at a suitable angle in Step 11A (S11A), the ROI determination unit 13 sets the IMT measurement range 212 in Step 12 (S12). In Step 13 (S13) the IMT measurement unit 14 performs IMT measurement based on the longitudinal cross-sectional image stored in the longitudinal cross-sectional image storage unit 5 during Step 3 (S03). The display control unit 15 controls the display 16 to display results of the IMT measurement. Steps 12 (S12) and 13 (S13) are the same as described for the ultrasound diagnostic device 1 relating to the first embodiment and explanation thereof is omitted.

<Effects>

Figure 15:
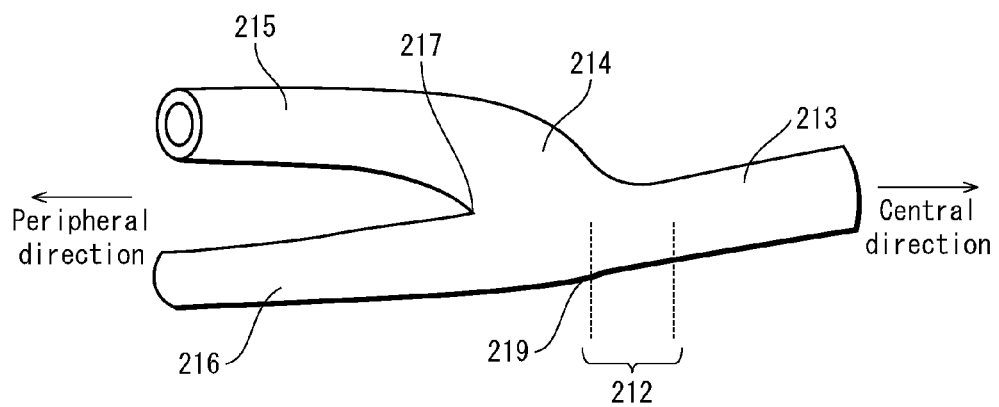
FIG. 15 is a perspective diagram illustrating structure of the carotid artery along the longitudinal direction.

Through the configuration described above, the ultrasound diagnostic device 1A relating to the second embodiment calculates relative angle of the ultrasound probe in the plane parallel to the carotid artery transverse cross-section based on central coordinates of respective cross-sections of the ICA 215, the ECA 216, and the CCA 213, extracted from respective transverse cross-sectional images 300 of a plurality of frames which are separated from each other by a predetermined number of frames. Consequently, the ultrasound diagnostic device 1A relating to the second embodiment enables more accurate calculation of relative angle of the ultrasound probe. As explained further above, Non-Patent Literature 1 recommends setting IMT measurement range 212 as a range extending from the CCA-bulb boundary 219 for 1 cm towards the CCA as illustrated in FIG. 15. Note that the present embodiment has a configuration in which relative angle of the ultrasound probe in the plane parallel to the carotid artery transverse cross-section is calculated using a transverse cross-sectional image 300 depicting the ICA 215 and the ECA 216, and also a transverse cross-sectional image 300 depicting the CCA 213, which is located on an opposite side of the CCA-bulb boundary 219 relative to the ICA 215 and the ECA 216. Consequently, the configuration described in the present embodiment enables more accurate calculation of relative angle of the ultrasound probe in proximity to the CCA-bulb boundary 219, compared to the first embodiment.

<<Modified Examples>>

Ultrasound diagnostic devices relating to embodiments of the present invention are described above, but the present invention is of course not limited to the ultrasound diagnostic devices explained in the embodiments. The ultrasound diagnostic devices explained as examples in the embodiments may also be modified in various ways such as described below.

(1) As illustrated in FIG. 2, the ultrasound diagnostic devices relating to the first embodiment and the second embodiment each use an oscillating ultrasound probe as the ultrasound probe 2. The aforementioned ultrasound diagnostic devices also each have a configuration including the transmission-reception processing unit 3 which performs transmission processing to supply a transmission signal in order that ultrasound is transmitted along a longitudinal cross-section of the carotid artery at each of a plurality of positions along a direction perpendicular to the longitudinal cross-section, and which performs reception processing in order to generate a reception signal for the longitudinal cross-section of the carotid artery at each of the positions, based on reflected ultrasound from the carotid artery which is received by the ultrasound probe 2.

The present invention is not however limited to the configuration described above and may have any configuration which enables acquisition of an ultrasound echo signal for a longitudinal cross-section and a transverse cross-section of a carotid artery.

For example, alternatively a 2D array ultrasound probe including a 2D array of transducers may be used. With the transducers applied against the skin surface such that transducers arranged in one arrangement direction thereof are aligned along the longitudinal direction of the carotid artery, an ultrasound beam can be scanned sequentially in another arrangement direction of the transducers in order to acquire ultrasound echo signals for longitudinal cross-sections and transverse cross-sections of the carotid artery.

In an alternative configuration, the transmission-reception processing unit 3 may perform transmission processing to supply a transmission signal in order that ultrasound is transmitted along a transverse cross-section of the carotid artery at a plurality of positions along a direction perpendicular to the transverse cross-section, and may perform reception processing in order to generate a reception signal for the carotid artery transverse cross-section at each of the positions based on ultrasound reflected from the carotid artery and received by the ultrasound probe 2.

(2) The ultrasound diagnostic devices relating to the first embodiment and the second embodiment each have a configuration in which the ROI determination unit 13 and the IMT measurement unit 14 perform IMT measurement based on a longitudinal cross-sectional image generated by the longitudinal cross-sectional image generation unit 4. Alternatively IMT measurement may be performed using a reception signal generated by the transmission-reception processing unit 3, without using a longitudinal cross-sectional image. Note that the longitudinal cross-sectional image generation unit 4 illustrated in FIG. 1 may be omitted in a configuration in which IMT measurement is performed using a reception signal. Also note that in such a configuration, the longitudinal cross-sectional image storage unit 5 is configured to store a reception signal from which a longitudinal cross-sectional image can be generated. In the configuration described above, Step 2 (S02) illustrated in FIG. 6 can be omitted and Step 3 (S03) is modified to a step of storing a reception signal from which a longitudinal cross-sectional image can be generated.

(3) The ultrasound diagnostic device 1 relating to the first embodiment has a configuration in which relative angle of the ultrasound probe in a plane parallel to a carotid artery transverse cross-section is calculated using a transverse cross-sectional image depicting the ICA 215 and the ECA 216, and the ultrasound diagnostic device 1A relating to the second embodiment has a configuration is which relative angle of the ultrasound probe in a plane parallel to a carotid artery transverse cross-section is calculated using a plurality of transverse cross-sectional images 300 depicting the ICA 215, the ECA 216, and the CCA 213. However, relative angle of the ultrasound probe in a plane parallel to a carotid artery transverse cross-section can be calculated from transverse cross-sectional images 300 depicting at least two out of the ICA 215, the ECA 216, and the CCA 213. As a consequence, in an alternative configuration transverse cross-sectional images 300 of two frames may be selected in the same way as in the second embodiment, and relative angle of the ultrasound probe may be calculated using central coordinates at which the CCA is depicted and also central coordinates at which either the ICA or the ECA is depicted. As described further above, Non-Patent Literature 1 recommends that IMT measurement range 212 is set as a range extending from the CCA-bulb boundary 219 for 1 cm towards the CCA 213 as illustrated in FIG. 15. In the alternative configuration described above, relative angle of the ultrasound probe in a plane parallel to a carotid artery transverse cross-section is calculated using a transverse cross-sectional image 300 depicting the ICA 215 or the ECA 216 and a transverse cross-sectional image 300 depicting the CCA 213, which are transverse cross-sectional images 300 acquired at opposite sides of the CCA-bulb boundary 219 relative to one another. Using transverse cross-sectional images 300 acquired at opposite sides of the CCA-bulb boundary 219 enables more accurate calculation of relative angle of the ultrasound probe in proximity to the CCA-bulb boundary 219.

Consequently, an ultrasound diagnostic device relating to the present modified example may comprise: a transmission-reception processor that performs transmission processing to supply a transmission signal to the ultrasound probe in order to drive the ultrasound probe to transmit ultrasound along a carotid artery cross-section at each of a plurality of positions along a direction perpendicular to the carotid artery cross-section, and that performs reception processing to generate a reception signal for the carotid artery cross-section at each of the positions, based on ultrasound reflected from the carotid artery and received by the ultrasound probe; a transverse cross-sectional image generator that generates a plurality of transverse cross-sectional images based on reception signals respectively generated at the positions, each of the transverse cross-sectional images depicting a carotid artery transverse cross-section that is perpendicular to a longitudinal direction of the carotid artery; a transverse cross-sectional image selector that selects, as a specific image from among the transverse cross-sectional images which are generated, a transverse cross-sectional image that depicts an internal carotid artery cross-section and an external carotid artery cross-section, and that selects, as an additional specific image from among the transverse cross-sectional images which are generated, a transverse cross-sectional image that depicts either one of a common carotid artery cross-section and a common carotid artery bulb cross-section; and a relative angle calculator that calculates a relative angle of the ultrasound probe with respect to the carotid artery in a plane parallel to the carotid artery transverse cross-section, based on coordinates at which either one of the internal carotid artery cross-section and the external carotid artery cross-section is depicted in the specific image, and coordinates at which the one of the common carotid artery cross-section and the common carotid artery bulb cross-section is depicted in the additional specific image.

(4) The ultrasound diagnostic devices relating to the first embodiment and the second embodiment each have a configuration in which the IMT measurement unit 14 performs IMT measurement on a portion of a longitudinal cross-sectional image of the carotid artery which is included in the ROI 211 determined by the ROI determination unit 13. In an alternative configuration, transverse cross-sectional images of a plurality of frames included in the ROI 211 determined by the ROI determination unit 13 may be acquired from the transverse cross-sectional image storage unit 7, and IMT measurement may be performed for each of the frames using the transverse cross-sectional image thereof. IMT can be measured using a vascular cross-sectional image which depicts a cross-section of a blood vessel along a transverse direction thereof, based, for example, on a method disclosed in International Publication No. WO2012/105162. Note that the bif 217 is detected and the ROI 211 is determined in the same way as in the ultrasound diagnostic devices relating to the first embodiment and the second embodiment. As a result of IMT measurement being performed using transverse cross-sectional images that each depict a central axis of the blood vessel and a region proximal thereto, IMT measurement is not affected by the transducer column becoming shifted from a position corresponding to the central axis of the blood vessel.

(5) The ultrasound diagnostic devices relating to the first embodiment and the second embodiment each have a configuration in which the property of the vascular wall which is measured using the reception signal for the cross-section included in the ROI is IMT, but the present invention is not limited to such a configuration and the property of the vascular wall of the carotid artery may alternatively be a property other than IMT. For example, alternatively the present invention may be used to measure characteristic properties of the carotid artery such as viscoelastic properties. Examples of viscoelastic properties include elasticity, strain, and viscosity.

The present invention is also effective in a situation in which, for example, presence of a carotid artery plaque—a major cause of cerebral infarction—or thickness thereof is measured as the property of the vascular wall of the carotid artery. In such a situation, measurement position of a plaque in a transverse cross-section of the carotid artery can be determined and change in size of the plaque can be observed by performing measurement at the same position during each measurement.

The present invention is also effective in a situation in which elastic modulus of the vascular wall of the carotid artery is measured as the property of the vascular wall by measuring temporal variation in IMT measurement values resulting from pulsations of the carotid artery. In such a situation, examination accuracy can be improved by performing measurement at the same position during each measurement.

<<Conclusion>>

As described above, an ultrasound diagnostic device relating to an embodiment of the present invention calculates relative angle of an ultrasound probe with respect to a carotid artery in a plane parallel to a carotid artery transverse cross-section, using one or more transverse cross-sectional images 300. The ultrasound diagnostic device also performs a judgment as to whether the relative angle which is calculated is a suitable angle and notifies an operator of results of the judgment. Upon judging that the relative angle is a suitable angle, the ultrasound diagnostic device proceeds to IMT measurement. Through the ultrasound diagnostic device described above, an IMT measurement range can be set at a suitable position in a vascular wall in the carotid artery transverse cross-section, increasing accuracy of diagnosis by enabling IMT measurement to be performed at the same position during each measurement. Furthermore, the ultrasound diagnostic device described above enables quick measurement of IMT through an operation which is simple even for an operator who does not possess a high degree of procedural skill.

<<Supplementary Explanation>>

The embodiments described above merely illustrated preferable examples of implementation of the present invention. Note that numbers, shapes, materials, configuration elements, arrangement and connection of configuration elements, steps, order of steps, and the like are merely examples and are not intended to in any way limit the present invention. Also note that configuration elements and steps explained in the embodiments but not included in independent claims indicating the most general concept of the present invention, are merely explained as optional configuration elements and steps which may be used in order to configure preferable embodiments.

In order to facilitate understanding of the present invention, drawings referred to in explanation of the embodiments do not necessarily illustrate configuration elements to scale. The present invention is not in any way limited by contents of the embodiments described above and various modifications are possible so long as such modifications do not deviate from the intended scope of the present invention.

Furthermore, in an ultrasound diagnostic device, parts such as circuit components and leads are mounted on a circuit board. Electrical wiring and electrical circuits may be implemented in various different configurations based on common knowledge in related technical fields. However, as such configurations are not directly related to explanation of the present invention, explanation of such configurations is omitted. Also note that the drawings are schematic diagrams and thus do not necessarily correspond exactly to matter illustrated thereby.

INDUSTRIAL APPLICABILITY

During measurement of a property of a vascular wall of a carotid artery, the present invention enables appropriate measurement and management of an angle at which an ultrasound probe, applied against skin surface of a neck, is positioned in a plane parallel to a carotid artery transverse cross-section, and thus enables quick and accurate measurement of the property of the vascular wall through an operation which can be simply performed even by an operator who does not possess a high degree of procedural skill. Therefore, the present invention can be widely applied to an ultrasound diagnostic device, a method for controlling an ultrasound diagnostic device, or the like.

REFERENCE SIGNS LIST 1, 1A ultrasound diagnostic device
2 ultrasound probe
3 transmission-reception processing unit
4 longitudinal cross-sectional image generation unit
5 longitudinal cross-sectional image storage unit
6 transverse cross-sectional image generation unit
7 transverse cross-sectional image storage unit
8 contour extraction unit
9 3D volume data storage unit
10, 10A transverse cross-sectional image selection unit
11, 11A relative angle calculation unit
12 relative angle judgment unit
13 ROI determination unit
14 IMT measurement unit
15 display control unit
16 display
100 vascular position detection sub-unit
101 vascular cross-section number detection sub-unit
102, 102A frame selection sub-unit
110, 110A central coordinates detection sub-unit
111, 111A angle calculation sub-unit
201 vascular wall
202 tunica intima
203 tunica media
204 lumen
205 tunica adventitia
206 intima-media complex
207 lumen-intima interface
208 media-adventitia interface
209 far-side wall 210 near-side wall
211 region of interest (ROI)
212 IMT measurement range
213 common carotid artery (CCA)
214 common carotid artery bulb (bulb)
215 internal carotid artery (ICA)
216 external carotid artery (ECA)
217 bifurcation of the common carotid artery (bif)
219 CCA-bulb boundary
300 transverse cross-sectional image
301, 302, 303 central coordinates
304 reference line
400, 400A controller

The invention claimed is:

1. An ultrasound diagnostic device to which an ultrasound probe is connectable, the ultrasound probe having a transducer column comprising a plurality of transducers, the ultrasound diagnostic device comprising:
- a transmission-reception processor that performs transmission processing to supply a transmission signal to the ultrasound probe in order to drive the ultrasound probe to transmit ultrasound along a longitudinal direction of a carotid artery at each of a plurality of positions along a direction perpendicular to the longitudinal direction of the carotid artery in a state in which the transducer column of the ultrasound probe is arranged along the longitudinal direction of the carotid artery, and that performs reception processing to generate reception signals along the longitudinal direction of the carotid artery at each of the positions in the direction perpendicular to the longitudinal direction, based on ultrasound reflected from the carotid artery and received by the ultrasound probe;
- a transverse cross-sectional image generator that generates a plurality of transverse cross-sectional images based on the reception signals respectively generated at the positions, each of the transverse cross-sectional images depicting a carotid artery transverse cross-section that is perpendicular to the longitudinal direction of the carotid artery, wherein each transverse cross-sectional image is generated from the reception signals acquired by a respective one of the plurality of transducers at the plurality of positions along the direction perpendicular to the longitudinal direction;
- a transverse cross-sectional image selector that selects, as a specific image from among the transverse cross-sectional images which are generated, a transverse cross-sectional image that depicts an internal carotid artery cross-section and an external carotid artery cross-section;
- a relative angle calculator that calculates a relative angle of the ultrasound probe with respect to the carotid artery in a plane parallel to the carotid artery transverse cross-section, based on coordinates at which the internal carotid artery cross-section and the external carotid artery cross-section are depicted in the specific image, wherein the relative angle calculator calculates the relative angle of the ultrasound probe based on central coordinates of the internal carotid artery cross-section and central coordinates of the external carotid artery cross-section depicted in the specific image;
- a longitudinal cross-sectional image generator that generates a longitudinal cross-sectional image of the carotid artery based on the reception signals acquired by the plurality of transducers at at least one of the positions, the longitudinal cross-sectional image depicting a carotid artery longitudinal cross-section; and
- a vascular wall property measurer that, upon a judgement that the calculated relative angle is a suitable angle, measures a property of a vascular wall of the carotid artery, using the longitudinal cross-sectional image.

2. The ultrasound diagnostic device of claim 1, wherein:
the transverse cross-sectional image selector further selects, as an additional specific image from among the transverse cross-sectional images which are generated, a transverse cross-sectional image that depicts either one of a common carotid artery cross-section and a common carotid artery bulb cross-section; and
the relative angle calculator calculates the relative angle of the ultrasound probe further based on coordinates at which the one of the common carotid artery cross-section and the common carotid artery bulb cross-section is depicted in the additional specific image.

3. The ultrasound diagnostic device of claim 2, wherein the relative angle calculator calculates the relative angle of the ultrasound probe based on the central coordinates of the internal carotid artery cross-section depicted in the specific image, the central coordinates of the external carotid artery cross-section depicted in the specific image, and central coordinates of the one of the common carotid artery cross-section and the common carotid artery bulb cross-section depicted in the additional specific image.

4. The ultrasound diagnostic device of claim 2, wherein the transverse cross-sectional image selector selects at least one out of the specific image and the additional specific image using, as a reference, a transverse cross-sectional image that depicts a bifurcation of a common carotid artery.

5. The ultrasound diagnostic device of claim 1, further comprising:
a notifier that notifies the relative angle calculated by the relative angle calculator to an operator.

6. The ultrasound diagnostic device of claim 1, wherein the transverse cross-sectional image selector selects the specific image using, as a reference, a transverse cross-sectional image that depicts a bifurcation of a common carotid artery.

7. The ultrasound diagnostic device of claim 6, wherein the transverse cross-sectional image selector determines the transverse cross-sectional image that depicts the bifurcation of the common carotid artery based on a number of carotid artery transverse cross-sections depicted in each of the plurality of transverse cross-sectional images which are generated.

8. The ultrasound diagnostic device of claim 6, further comprising:
a relative angle judger that performs the judgment of whether the relative angle is the suitable angle.

9. The ultrasound diagnostic device of claim 8, wherein the relative angle judger stores therein a preset reference angle and judges that the relative angle is the suitable angle when the relative angle is within a predetermined range of the reference angle.

10. The ultrasound diagnostic device of claim 8, further comprising:
a notifier that notifies results of the judgment performed by the relative angle judger to an operator.

11. The ultrasound diagnostic device of claim 8, further comprising:
an ROI determiner that, upon the relative angle judger judging that the relative angle is the suitable angle, determines an ROI that defines a measurement range for IMT measurement, using, as a reference, the transverse cross-sectional image that depicts the bifurcation of the common carotid artery;

wherein the vascular wall property measurer comprises an IMT measurer that measures, in the ROI, IMT as the property of the vascular wall of the carotid artery using the longitudinal cross-sectional image.

12. The ultrasound diagnostic device of claim 1, further comprising the ultrasound probe which has the transducer column comprising the plurality of transducers, wherein the plurality of transducers are arranged along a column direction.

13. An ultrasound diagnostic device to which an ultrasound probe is connectable, the ultrasound probe having a transducer column comprising a plurality of transducers, the ultrasound diagnostic device comprising:

a transmission-reception processor that performs transmission processing to supply a transmission signal to the ultrasound probe in order to drive the ultrasound probe to transmit ultrasound along a longitudinal direction of a carotid artery at each of a plurality of positions along a direction perpendicular to the longitudinal direction of the carotid artery in a state in which the transducer column of the ultrasound probe is arranged along the longitudinal direction of the carotid artery, and that performs reception processing to generate reception signals along the longitudinal direction of the carotid artery at each of the positions in the direction perpendicular to the longitudinal direction, based on ultrasound reflected from the carotid artery and received by the ultrasound probe;

a transverse cross-sectional image generator that generates a plurality of transverse cross-sectional images based on the reception signals respectively generated at the positions, each of the transverse cross-sectional images depicting a carotid artery transverse cross-section that is perpendicular to the longitudinal direction of the carotid artery, wherein each transverse cross-sectional image is generated from the reception signals acquired by a respective one of the plurality of transducers at the plurality of positions along the direction perpendicular to the longitudinal direction;

a transverse cross-sectional image selector that selects, as a specific image from among the transverse cross-sectional images which are generated, a transverse cross-sectional image that depicts an internal carotid artery cross-section and an external carotid artery cross-section, and that selects, as an additional specific image from among the transverse cross-sectional images which are generated, a transverse cross-sectional image that depicts either one of a common carotid artery cross-section and a common carotid artery bulb cross-section;

a relative angle calculator that calculates a relative angle of the ultrasound probe with respect to the carotid artery in a plane parallel to the carotid artery transverse cross-section, based on coordinates at which either one of the internal carotid artery cross-section and the external carotid artery cross-section is depicted in the specific image, and coordinates at which the one of the common carotid artery cross-section and the common carotid artery bulb cross-section is depicted in the additional specific image, wherein the relative angle calculator calculates the relative angle of the ultrasound probe based on central coordinates of the one of the internal carotid artery cross-section and the external carotid artery cross-section depicted in the specific image, and central coordinates of the one of the common carotid artery cross-section and the common carotid artery bulb cross-section depicted in the additional specific image;

a longitudinal cross-sectional image generator that generates a longitudinal cross-sectional image of the carotid artery based on the reception signals acquired by the plurality of transducers at at least one of the positions, the longitudinal cross-sectional image depicting a carotid artery longitudinal cross-section; and a vascular wall property measurer that, upon a judgement that the calculated relative angle is a suitable angle, measures a property of a vascular wall of the carotid artery, using the longitudinal cross-sectional image.

14. The ultrasound diagnostic device of claim 13, further comprising:

a notifier that notifies the relative angle calculated by the relative angle calculator to an operator.

15. The ultrasound diagnostic device of claim 13, wherein the relative angle calculator calculates the relative angle of the ultrasound probe based on the central coordinates of both of the internal carotid artery cross-section and the external carotid artery cross-section depicted in the specific image, and the central coordinates of the one of the common carotid artery cross-section and the common carotid artery bulb cross-section depicted in the additional specific image.

16. The ultrasound diagnostic device of claim 13, wherein the transverse cross-sectional image selector selects at least one out of the specific image and the additional specific image using, as a reference, a transverse cross-sectional image that depicts a bifurcation of a common carotid artery.

17. The ultrasound diagnostic device of claim 16, further comprising:

a relative angle judger that performs the judgment of whether the relative angle is the suitable angle;

an ROI determiner that, upon the relative angle judger judging that the relative angle is the suitable angle, determines an ROI that defines a measurement range for IMT measurement, using, as a reference, the transverse cross-sectional image that depicts the bifurcation of the common carotid artery; and wherein the vascular wall property measurer comprises an IMT measurer that measures, in the ROI, IMT as the property of the vascular wall of the carotid artery using the longitudinal cross-sectional image.

18. A method for controlling an ultrasound diagnostic device to which an ultrasound probe is connectable, the ultrasound probe having a transducer column comprising a plurality of transducers, the method comprising:

performing transmission processing to supply a transmission signal to the ultrasound probe in order to drive the ultrasound probe to transmit ultrasound along a longitudinal direction of a carotid artery at each of a plurality of positions along a direction perpendicular to the longitudinal direction of the carotid artery in a state in which the transducer column of the ultrasound probe is arranged along the longitudinal direction of the carotid artery, and performing reception processing to generate reception signals along the longitudinal direction of the carotid artery at each of the positions in the direction perpendicular to the longitudinal direction, based on ultrasound reflected from the carotid artery and received by the ultrasound probe;

generating a plurality of transverse cross-sectional images based on the reception signals respectively generated at the positions, each of the transverse cross-sectional images depicting a carotid artery transverse cross-section that is perpendicular to the longitudinal direction of the carotid artery, wherein each transverse cross-sectional image is generated from the reception signals acquired by a respective one of the plurality of transducers at the plurality of positions along the direction perpendicular to the longitudinal direction;

selecting, as a specific image from among the transverse cross-sectional images which are generated, a transverse cross-sectional image that depicts an internal carotid artery cross-section and an external carotid artery cross-section;

calculating a relative angle of the ultrasound probe with respect to the carotid artery in a plane parallel to the carotid artery transverse cross-section, based on coordinates at which the internal carotid artery cross-section and the external carotid artery cross-section are depicted in the specific image, wherein the relative angle of the ultrasound probe is calculated based on central coordinates of the internal carotid artery cross-section and central coordinates of the external carotid artery cross-section depicted in the specific image;

generating a longitudinal cross-sectional image of the carotid artery based on the reception signals acquired by the plurality of transducers at at least one of the positions, the longitudinal cross-sectional image depicting a carotid artery longitudinal cross-section; and upon a judgement that the calculated relative angle is a suitable angle, measuring a property of a vascular wall of the carotid artery, using the longitudinal cross-sectional image.

19. The method of claim 18, further comprising:
selecting, as an additional specific image from among the transverse cross-sectional images which are generated, a transverse cross-sectional image that depicts either one of a common carotid artery cross-section and a common carotid artery bulb cross-section,
wherein the relative angle of the ultrasound probe is calculated further based on coordinates at which the one of the common carotid artery cross-section and the common carotid artery bulb cross-section is depicted in the additional specific image.

20. The method of claim 18, further comprising:
notifying the relative angle which is calculated to an operator.

21. The method of claim 18, wherein the specific image is selected using, as a reference, a transverse cross-sectional image that depicts a bifurcation of a common carotid artery, and the method further comprises:
judging whether the relative angle is the suitable angle;
determining, when the relative angle is judged to be the suitable angle, an ROI that defines a measurement range for IMT measurement, using, as a reference, the transverse cross-sectional image that depicts the bifurcation of the common carotid artery; and
measuring, in the ROI, IMT as the property of the vascular wall of the carotid artery using the longitudinal cross-sectional image.

22. A method for controlling an ultrasound diagnostic device to which an ultrasound probe is connectable, the ultrasound probe having a transducer column comprising a plurality of transducers, the method comprising:

performing transmission processing to supply a transmission signal to the ultrasound probe in order to drive the ultrasound probe to transmit ultrasound along a longitudinal direction of a carotid artery at each of a plurality of positions along a direction perpendicular to the longitudinal direction of the carotid artery in a state in which the transducer column of the ultrasound probe is arranged along the longitudinal direction of the carotid artery, and performing reception processing to generate reception signals along the longitudinal direction of the carotid artery at each of the positions in the direction perpendicular to the longitudinal direction, based on ultrasound reflected from the carotid artery and received by the ultrasound probe;

generating a plurality of transverse cross-sectional images based on the reception signals respectively generated at the positions, each of the transverse cross-sectional images depicting a carotid artery transverse cross-section that is perpendicular to the longitudinal direction of the carotid artery, wherein each transverse cross-sectional image is generated from the reception signals acquired by a respective one of the plurality of transducers at the plurality of positions along the direction perpendicular to the longitudinal direction;

selecting, as a specific image from among the transverse cross-sectional images which are generated, a transverse cross-sectional image that depicts an internal carotid artery cross-section and an external carotid artery cross-section, and selecting, as an additional specific image from among the transverse cross-sectional images which are generated, a transverse cross-sectional image that depicts either one of a common carotid artery cross-section and a common carotid artery bulb cross-section;

calculating a relative angle of the ultrasound probe with respect to the carotid artery in a plane parallel to the carotid artery transverse cross-section, based on coordinates at which either one of the internal carotid artery cross-section and the external carotid artery cross-section is depicted in the specific image, and coordinates at which the one of the common carotid artery cross-section and the common carotid artery bulb cross-section is depicted in the additional specific image, wherein the relative angle of the ultrasound probe is calculated based on central coordinates of the one of the internal carotid artery cross-section and the external carotid artery cross-section depicted in the specific image, and central coordinates of the one of the common carotid artery cross-section and the common carotid artery bulb cross-section depicted in the additional specific image;

generating a longitudinal cross-sectional image of the carotid artery based on the reception signals acquired by the plurality of transducers at at least one of the positions, the longitudinal cross-sectional image depicting a carotid artery longitudinal cross-section; and upon a judgement that the calculated relative angle is a suitable angle, measuring a property of a vascular wall of the carotid artery, using the longitudinal cross-sectional image.

* * * * *